(12) United States Patent
Johnson

(10) Patent No.: US 10,663,467 B2
(45) Date of Patent: May 26, 2020

(54) METHODS AND ANTISERA FOR ISOLATING AND IDENTIFYING SUBSETS OF CD8 T CELLS

(71) Applicant: Raymond M. Johnson, Indianapolis, IN (US)

(72) Inventor: Raymond M. Johnson, Indianapolis, IN (US)

(*) Notice: Subject to any disclaimer, the term of this patent is extended or adjusted under 35 U.S.C. 154(b) by 0 days.

(21) Appl. No.: 15/627,755

(22) Filed: Jun. 20, 2017

(65) Prior Publication Data

US 2017/0363626 A1    Dec. 21, 2017

Related U.S. Application Data

(63) Continuation-in-part of application No. 14/642,546, filed on Mar. 9, 2015, now Pat. No. 9,683,262, which
(Continued)

(51) Int. Cl.
*G01N 33/569*    (2006.01)
*G01N 33/68*     (2006.01)
(Continued)

(52) U.S. Cl.
CPC ....... *G01N 33/56972* (2013.01); *C07K 16/28* (2013.01); *C12N 5/0087* (2013.01); *C12N 5/0638* (2013.01); *C12Q 1/6881* (2013.01); *C12Q 1/6883* (2013.01); *G01N 33/505* (2013.01); *G01N 33/6869* (2013.01); *C07K 2317/24* (2013.01); *C07K 2317/34* (2013.01); *C07K 2317/76* (2013.01); *C12Q 2600/158* (2013.01); *G01N 2333/295* (2013.01);
(Continued)

(58) Field of Classification Search
CPC ............. C12N 5/0087; C12N 5/0638; C12Q 2600/158; C12Q 1/6881; C12Q 1/6883; C07K 2317/34; C07K 16/28; C07K 2317/76; C07K 2317/24; G01N 2333/295; G01N 33/56972; G01N 33/6869; G01N 33/505; G01N 2333/5409; G01N 2333/5437; G01N 2800/26; G01N 2333/70517
See application file for complete search history.

(56) References Cited

PUBLICATIONS

Igietseme et al. Role for CD8+ T cells in antichlamydial immunity defined by Chlamydia-specific T-lymphocyte clones. Infect Immun 62: 5195-5197 (1994). USA.
Jayarapu et al. Chlamydia muridarum-specific CD4 T-cell clones recognize infected reproductive tract epithelial cells in an interferon-dependent fashion. Infect Immun 77: 4469-4479 (2009). USA.
Johnson et al. An atypical CD8 T-cell response to Chlamydia muridarum genital tract infections includes T cells that produce interleukin-13. Immunology 142: 248-257 (2014). USA.
(Continued)

*Primary Examiner* — Jana A Hines
(74) *Attorney, Agent, or Firm* — Reichel Stohry Dean LLP; Natalie J. Dean

(57) ABSTRACT

Methods for identifying and isolating CD8 T cells that produce interleukin-13 upon activation are provided. The present methods leverage one or more newly-identified biomarkers to identify such CD8 T cells and, in certain cases, sort the same. Certain methods comprise obtaining a sample from a mammal, quantifying a level of expression of one or more biomarkers therein, and determining if the level of expression is elevated as compared, wherein an elevated expression level is indicative of an active disease state. Antisera and antibodies are also provided. In particular, an anti-C10orf128 antiserum formulated against a particular peptide is provided, such anti-C10orf128 antiserum characterized in that it identifies a subset of CD8 T cells that produce interleukin-13 upon activation.

13 Claims, 13 Drawing Sheets

Specification includes a Sequence Listing.

Related U.S. Application Data is a continuation-in-part of application No. 14/215,144, filed on Mar. 17, 2014, now abandoned.

(60) Provisional application No. 61/950,386, filed on Mar. 10, 2014, provisional application No. 61/787,048, filed on Mar. 15, 2013.

(51) Int. Cl.
    *G01N 33/50*     (2006.01)
    *C07K 16/28*     (2006.01)
    *C12Q 1/6881*    (2018.01)
    *C12N 5/0783*    (2010.01)
    *C12N 5/00*      (2006.01)
    *C12Q 1/6883*    (2018.01)

(52) U.S. Cl.
    CPC .............. *G01N 2333/5409* (2013.01); *G01N 2333/5437* (2013.01); *G01N 2333/70517* (2013.01); *G01N 2800/26* (2013.01)

(56) References Cited

PUBLICATIONS

Fuschiotti et al. Interleukin-13-producing CD8+ T cells mediate dermal fibrosis in patients with systemic sclerosis. Arthritis Rheum 65: 236-246 (2013). USA.

Igietseme et al. Role of T lymphocytes in the pathogenesis of Chlamydia disease. J Infect Dis 200: 926-934 (2009). USA.

Murthy et al. Tumor necrosis factor alpha production from CD8+ T cells mediates oviduct pathological sequelae following primary genital Chlamydia muridarum infection. Infect Immun 79: 2928-2935 (2011). USA.

Johnson et al. An atypical CD8 T-cell response to Chlamydia muridarum genital tract infections includes T cells that product interleukin-13. Immunology 142: 248-257 (2014). USA.

Fuschiotti et al. Effector CD8+ T cells in systemic sclerosis patients produce abnormally high levels of interleukin-13 associated with increased skin fibrosis. Arthritis Rheum 60: 1119-1128 (2009). USA.

Fuschiotti et al. Interleukin-13-producing CD8+ T cells mediate dermal fibrosis in patients with systemic sclerosis. Arthritis Rheum 65: 236-246 (2013).

| Gene Symbol | p-value (CD8IL13+ vs. CD8IL13- and allo CD8) | Fold-Change (CD8IL13+ vs. CD8IL13- and allo CD8) | p-value (CD8IL13+ vs. CD8IL13-) | Fold-Change (CD8IL13+ vs. CD8IL13-) | p-value (CD8IL13+ vs. allo CD8) | Fold-Change (CD8IL13+ vs. allo CD8) | same direction | sig | >3 |
|---|---|---|---|---|---|---|---|---|---|
| 1810011H11Rik | 1.52E-15 | 22.31 | 2.12E-15 | 24.85 | 8.19E-14 | 20.03 | Y | 1 | 1 |
| Amelx | 8.75E-12 | 10.68 | 1.57E-10 | 7.75 | 4.13E-11 | 14.71 | Y | 1 | 1 |
| Dclk3 | 8.80E-12 | 6.20 | 3.77E-11 | 5.73 | 1.37E-10 | 6.72 | Y | 1 | 1 |
| Mtmr7 | 8.29E-09 | 5.40 | 5.86E-09 | 6.24 | 5.72E-07 | 4.67 | Y | 1 | 1 |
| Ccr8 | 2.15E-08 | 8.90 | 4.58E-08 | 8.89 | 4.49E-07 | 8.91 | Y | 1 | 1 |
| Arntl | 5.51E-07 | 6.84 | 3.00E-08 | 12.80 | 5.00E-04 | 3.65 | Y | 1 | 1 |
| Sulf2 | 1.84E-06 | 10.10 | 2.14E-04 | 4.84 | 1.12E-06 | 21.07 | Y | 1 | 1 |
| Prl2c5 | 9.94E-05 | 8.88 | 2.06E-04 | 8.54 | 7.44E-04 | 9.24 | Y | 1 | 1 |
| Hpgds | 1.20E-04 | 8.11 | 4.49E-04 | 6.86 | 5.25E-04 | 9.60 | Y | 1 | 1 |

FIG. 6

| Gene Symbol | gene title |
|---|---|
| *1810011H11Rik* | uncharacterized protein LOC69069 precursor |
| *Amelx* | amelogenin X chromosome |
| *Dclk3* | doublecortin-like kinase 3 |
| *Mtmr7* | myotubularin related protein 7 |
| *Ccr8* | chemokine (C-C motif) receptor 8 |
| *Arntl* | aryl hydrocarbon receptor nuclear translocator-like |
| *Sulf2* | sulfatase 2 |
| *Prl2c5* | prolactin family 2, subfamily c, member 5 |
| *Hpgds* | hematopoietic prostaglandin D synthase |

METHODS AND ANTISERA FOR ISOLATING AND IDENTIFYING SUBSETS OF CD8 T CELLS

PRIORITY

This application is related to, claims the priority benefit of, and is a U.S. continuation-in-part patent application U.S. Nonprovisional patent application Ser. No. 14/642,546, filed Mar. 9, 2015 and which issues as U.S. Pat. No. 9,683,262 on Jun. 20, 2017, which (a) is related to, claims the priority benefit of, and is a continuation-in-part application of U.S. patent application Ser. No. 14/215,144, filed Mar. 17, 2014, which is related to and claims the priority benefit of U.S. Provisional Application Ser. No. 61/787,048, filed Mar. 15, 2013; (b) is related to and claims the priority benefit of U.S. Provisional patent application Ser. No. 61/950,386, filed Mar. 10, 2014; and (c) is related to and contains the disclosure of U.S. Provisional Application Ser. No. 62/126,161, filed Feb. 27, 2015. The contents of each of the aforementioned applications are hereby expressly incorporated by reference in their entireties into this disclosure.

STATEMENT REGARDING FEDERALLY SPONSORED RESEARCH

This invention was made with government support under R01 AI070514 and R01 AI113103 awarded by the National Institutes of Health. The United States Government has certain rights in the invention.

BACKGROUND

Systemic Sclerosis

Systemic sclerosis (also known as SSc or scleroderma) is a severe rheumatologic illness with inflammation of small and medium sized vessels throughout the body that causes cycles of ischemic injury, neovascularization, and progressive scarring in the skin and visceral organs. Current diagnostic criteria are dependent on physical findings combined with autoantibodies (ANA combined with Scl-70 and anti-centromere B) that are not believed to be directly involved in the pathogenesis of the disease. In addition to suboptimal diagnostic tests for systemic sclerosis, there is no effective therapy currently available for this disease.

Investigations into systemic sclerosis have not identified the cause of a presumed autoimmune attack on small and medium sized vessels, but have identified the effector cell type responsible for the immune-mediated damage. In 2009, investigators showed that systemic sclerosis patients have a unique CD8 T cell population in peripheral blood and skin that produce the protein interleukin 13 (IL-13) when activated (hereafter referred to as CD8IL-13 T cells). In addition, studies have shown that dermal fibroblasts exposed to culture supernatants from scleroderma CD8 T cells produce collagen (which results in scarring) through a mechanism dependent on IL-13 and tumor necrosis factor beta (TGF-beta), which is the master cytokine involved in collagen production and scarring. Others investigating mechanisms of scarring in other experimental systems have shown that the combination of tumor necrosis factor alpha (TNF-alpha) and IL-13 causes stromal cells to make TGF-beta. Unfortunately, however, the IL-13 producing CD8 T cells in human studies could only be identified by activation, fixation/permeabilization/intracellular cytokine staining for IL-13. That processing requirement has conventionally rendered the accessible CD8IL-13 T cell population unusable for advanced investigations such as gene expression micro array analyses.

Chlamydia Infection

Chlamydia infection is the most common sexually transmitted disease, responsible for about 2.8 million cases a year in the US. Untreated Chlamydia infections can ascend into the upper reproductive tract causing scarring and fibrosis that result in infertility and ectopic pregnancies. Fibrosis is a major contributor to scarring (the shared biologic trait shared with scleroderma) caused by Chlamydia infection.

Working in the mouse model for Chlamydia trachomatis infections, the inventor of the present application developed unique methodologies for cloning antigen-specific T cell clones based on unconventional antigen preparations and antigen presenting cells. Chlamydia infections of the genital tract are clinically important because the infection-promoted scarring of the genital tract that leads to infertility and ectopic pregnancy.

It is conventionally known that T cells, and specifically CD8 T cells, are the predominant inflammatory infiltrate in affected tissue thought to produce cytokines that drive the synthesis of extracellular matrix proteins by fibroblasts that results in excess fibrosis. Research in the mouse model for Chlamydia genital tract infections has shown unambiguously that scarring and infertility are mediated by CD8 T cells. Perhaps more specifically, the inventor hereof has shown in the mouse model that the CD8 T cell response to Chlamydia genital tract infections is atypical and includes the antigen-specific CD8IL-13 T cells that also produce TNF-alpha when activated.

As previously noted, although human CD8+ T cells expressing IL-13 have been described in humans, they unfortunately are not currently a usable tool to study the biology, protein, and gene expression in these cells, nor to screen prospective therapeutics. This is in large part because convention human CD8IL-13 T cell subset biomarkers do not allow for the practicable purification of viable CD8IL-13 T cells required to perform the genomic and functional studies needed to develop improved diagnostic tests, test therapeutic drugs, and identify new therapeutic targets.

Accordingly, and especially given the huge impact that both Chlamydia infections and scleroderma have on human health and the problems that exist with currently available treatments for both conditions, there is a pressing need for an increased understanding of the role of CD8 T cells in the human immune system and, more specifically, for a useful tool to study CD8IL-13 T cells. Similarly, a need exists to identify biomarkers for human CD8IL-13 T cells, with such biomarkers capable of facilitating viable cell purification protocols such that genomic and functional studies may be performed thereon. In this manner, meaningful diagnostic testing and therapeutic interventions could be screened for the purposes of (a) vaccine development, (b) diagnosing and treating pathological scarring during Chlamydia infections, and (c) diagnosing and treating pathological scarring in patients with scleroderma. As provided herein, gene expression microarray experiments utilizing murine CD8IL-13 and conventional CD8 T cell clones have been used to identify biomarkers for human CD8IL-13 T cells. The inventor of this application has identified that the human homolog (C10orf128) of the murine cell surface biomarker for CD8IL-13 T cells (1810011H11Rik) is expressed in the circulating CD8 T cell pool of patients with scleroderma, and can be practicably used to purify the desired CD8IL-13 T cell subset from the peripheral blood of human subjects.

BRIEF SUMMARY

The present disclosure provides novel methods, antisera, and antibodies for isolating and/or identifying subsets of CD8 T cells, particularly those that produce interleukin-13 (CD8IL13) upon activation. Additionally, methods for leveraging these novel methodologies in a clinical context are provided—for example, methods for analyzing the efficacy of small molecules and other compounds for use in therapeutic applications with respect to disrupting CD8IL13 pathophysiology, as well as methods for diagnosing and treating disease states mediated by CD8IL13 T cells.

In at least one embodiment of the present disclosure a method for identifying a subset of CD8 T cells that produce interleukin-13 upon activation is provided. In such embodiments, the method comprises: obtaining a sample from a mammal, the sample comprising a population of CD8 T cells, and quantifying a level of expression of one or more biomarkers in the isolated subset of CD8 T cells. In such cases, each of the one or more biomarkers may be selected from a group consisting of C10orf128, IL-13, IL-5, Arntl, Cep85L, Amelx, Clc, and Alox5. Additionally, in at least one exemplary embodiment, the sample may be peripheral blood and the mammal may be a human.

In at least one embodiment, the subset of CD8 T cells that produce interleukin-13 upon activation are used to test small molecule inhibitors for disrupting CD8IL-13 pathophysiology. Additionally or alternatively, the method may further comprise analyzing a measured effect/parameter or parameter in connection with the application of one or more small molecule inhibitors to a subset of CD8 T cells that product interleukin-13 upon activation, wherein the subset of CD8 T cells is within the population of CD8 T cells and the measured effect/parameter relates to a pathophysiology in the mammal mediated by the subset of CD8 T cells that produce interleukin-13 upon activation. In particular, the measured parameter may relate to disrupting the pathophysiology in the mammal if the one or more small molecule inhibitors is determined effective.

In at least one embodiment, quantifying a level of expression of one or more biomarkers may further comprise extracting ribonucleic acid or protein from the population of CD8 T cells and quantifying a level of messenger ribonucleic acid or protein for at least one of the one or more biomarkers in the extracted ribonucleic acid or protein. In such cases, quantifying a level of messenger ribonucleic acid or protein for at least one of the one or more biomarkers may be performed using flow cytometry gated on CD8 T cells, for example.

In certain embodiments of the method, the sample may comprise blood serum, the mammal may comprise a human, and one or more biomarkers may comprise Clc. There, the method may also comprise the step of determining if the blood serum has an elevated level of Clc as compared to a healthy control, where an elevated blood serum level of Clc is indicative of the mammal experiencing a rheumatologic disease state. In alternative embodiments, at least one of the one or more biomarkers may comprise C10orf128, and quantifying the level of expression of one or more biomarkers may utilize an anti-C10orf128 anti-serum. The anti-C10orf128 anti-serum may be made against a peptide having an amino acid sequence comprising SEQ ID No. 1 or a functional equivalent, variant, or fragment thereof.

The methods of the present disclosure may also comprise the step of determining if the population of CD8 T cells express an elevated level of the one or more biomarkers as compared to a healthy control. There, in at least one embodiment, an elevated level of expression of the one or more biomarkers is indicative of a presence of a subset of CD8 T cells that produce interleukin-13 upon activation within the population of CD8 T cells and the mammal experiencing a disease state mediated by the subset of CD8 T cells that produce interleukin-13 upon activation. Such a disease state may comprise scleroderma, for example. Furthermore, it may be indicative that the disease state is scleroderma when the elevated level of expression of the one or more biomarkers comprises a value greater than or equal to 1.5 times that of a value of the healthy control.

The methods hereof may further comprise the step of administering a therapeutically effective dose of a compound. In at least one embodiment, the compound may comprise an Alox5 inhibitor. Additionally or alternatively, the compound may comprise antibodies to C10orf128 to treat the scleroderma.

Antiserums are also provided. In at least one embodiment, an anti-C10orf128 antiserum formulated against a peptide having an amino acid sequence comprising SEQ ID No. 1 or a functional equivalent, variant, or fragment thereof is disclosed. In such cases, the anti-C10orf128 antiserum may be characterized in that it identifies a subset of CD8 T cells that produce interleukin-13 upon activation. Additionally, the antiserums hereof may additionally comprise a carrier protein attached to the peptide. In at least one exemplary embodiment, the antiserum comprises a rabbit antiserum. Additionally or alternatively, the antiserum may comprise a monoclonal antibody derived from a mammalian animal host (and optionally humanized using recombinant DNA technologies) or a C10orf128-specific immunoglobulin comprising messenger ribonucleic acid or protein sequences determined by molecular techniques.

Additional methods for identifying a subset of CD8 T cells that produce interleukin-13 upon activation are also provided, such methods comprising the steps of: obtaining a blood sample from a mammal, the blood sample comprising a population of CD8 T cells; quantifying a level of expression of one or more biomarkers in the population of CD8 T cells using an anti-C10orf128 anti-serum; and determining if the population of CD8 T cells express an elevated level of the one or more biomarkers as compared to a healthy control. In at least one exemplary embodiment, an elevated level of expression of the one or more biomarkers is indicative of a presence of a subset of CD8 T cells that produce interleukin-13 upon activation within the population of CD8 T cells and the mammal experiencing a disease state mediated by the subset of CD8 T cells. Additionally or alternatively, the anti-C10orf128 anti-serum may be formulated against a peptide having an amino acid sequence comprising SEQ ID No. 1 or a functional equivalent, variant, or fragment thereof, the anti-C10orf128 antiserum characterized in that it identifies a subset of CD8 T cells that produce interleukin-13 upon activation. Still further, each of the one or more biomarkers is selected from a group consisting of: C10orf728, IL-13, IL-5, Arntl, Cep8L, Amelx, Clc, and Alox5.

BRIEF DESCRIPTION OF THE SEQUENCE LISTING

SEQ ID NO. 1 is a human peptide representing the extracellular domain of C10orf128 and having an amino acid sequence comprising QVLATGKTPGAEIDFKY (or a functional equivalent, variant or fragment thereof) which, according to the subject disclosure, can be used to generate antibodies that bind the cell surface domain of the C10orf128, and thereby, in conjunction with CD8-specific antibodies, identify CD8IL-13 T cells.

SEQ ID NO. 2 is an artificial peptide representing a scrambled version of SEQ ID NO. 1 and having an amino acid sequence comprising QVLADIEAGPTKGTYKF (or a functional equivalent, variant, or fragment thereof) which, according to the subject disclosure, can be used to remove unwanted, non-specific antibodies from polyclonal antibody preparations by cross absorption, thereby improving the specificity and utility of antibodies made to SEQ ID NO. 1.

In addition to the foregoing, a written Sequence Listing for the above-described sequences is appended hereto and the same Sequence Listing is provided in computer readable form encoded in a file filed herewith and herein incorporated by reference. The information recorded in computer readable form is identical to the written Sequence Listing provided herein, pursuant to 37 C.F.R. § 1.821(f).

BRIEF DESCRIPTION OF THE DRAWINGS

The present invention will be better understood and features, aspects and advantages other than those set forth above will become apparent in light of the following detailed description thereof. Such detailed description makes reference to the following drawings, wherein.

Figure 1:
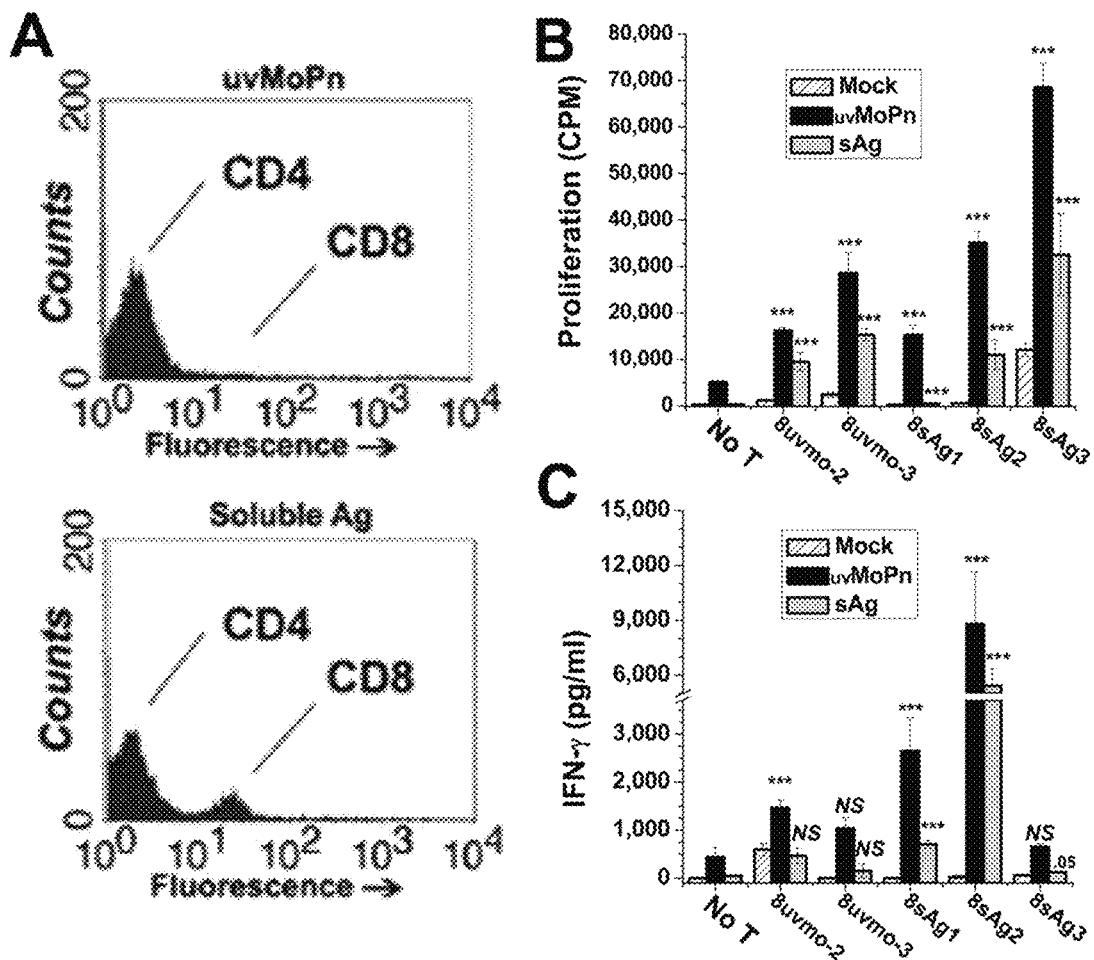
FIG. 1 shows graphical data supporting that *Chlamydia*-specific CD8 T cell clones are successfully recovered from immune mice using the novel methodology based on immune antigen presentation set forth herein.

Subpart A of FIG. 1) Shows graphical data of T cell counts. CD8 T cells are a minor subset in bulk *Chlamydia*-specific T cell populations expanded ex vivo using conventional irradiated naive splenocytes as antigen presenting cells (<1%; see FIG. 5): however, using irradiated immune splenocytes pulsed with either UV-inactivated *C. muridarum* (uvMoPn) or soluble antigen (soluble Ag) allowed expansion of *Chlamydia*-specific CD8 T cells (results for expansion of CD8 T cells pulsed with uvMoPn shown in upper graph and CD8 T cells pulsed with soluble Ag shown in lower graph). Soluble antigen was more effective than uvMoPn for CD8 T cell expansion. This discovery led to recovery of *Chlamydia*-specific CD8 T cell populations and subsequent isolation of CD8IL-13 T cell clones.

Subpart B of FIG. 1) Shows bar graph data representative of the specificity of five CD8 T cell clones derived using irradiated immune splenocytes as feeder APC. Each T cell clone was activated with irradiated (2000 rad) immune splenocytes mock-pulsed, uvMoPn-pulsed, and EB-depleted antigen (sAg)-pulsed. At 36 h culture supernatants were harvested and 3H-thymidine added; wells were harvested at 48 h to score proliferation. Proliferation shown in counts per minute (CPM).

Figure 2A:
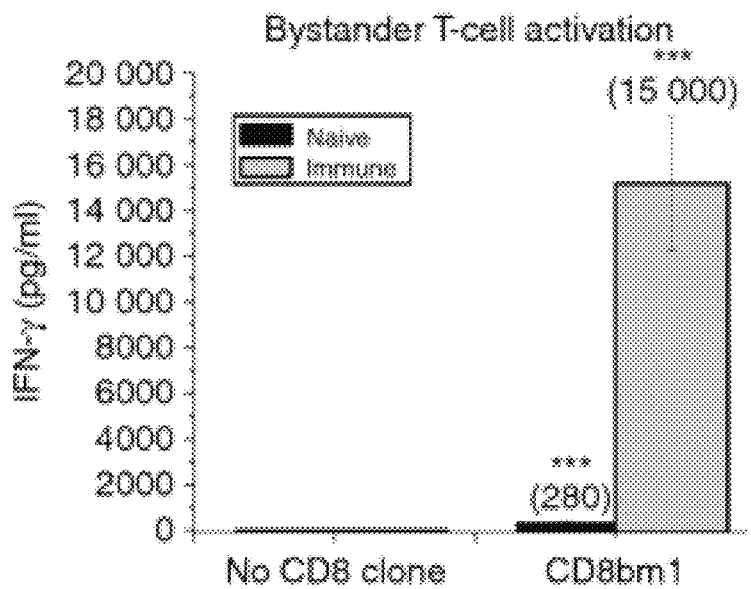

Subpart C of FIG. 1) Shows bar graph data representative of IFN-γ production for same experiments in subpart B of FIG. 1 as determined by ELISA. Data are Means and SD for one experiment done as quadruplicates. For each T cell clone the experimental wells were compared to its mock-pulsed control and to the APC only control (No T) for the relevant antigen. The higher p value of those two comparisons (the least significant) was assigned and graphed. *=p value <0.05; =p value <0.005: *=p value <0.0005. Conclusion: All CD8 T cell clones recognized *Chlamydia* antigen-pulsed immune splenocytes as measured by proliferation. IFN-γ production, or both; and FIG. 2A shows graphical major histocompatibility complex mapping data supporting that MHC mapping cannot be done with immune splenocytes as antigen presenting cells because of a bystander effect as demonstrated by non-specific activation of alloreactive CD8 T cell clone CD8bm1 as measured by IFN-gamma release when immune, but not naïve, irradiated splenocytes are pulsed with *Chlamydia* antigen.

Figure 2B:
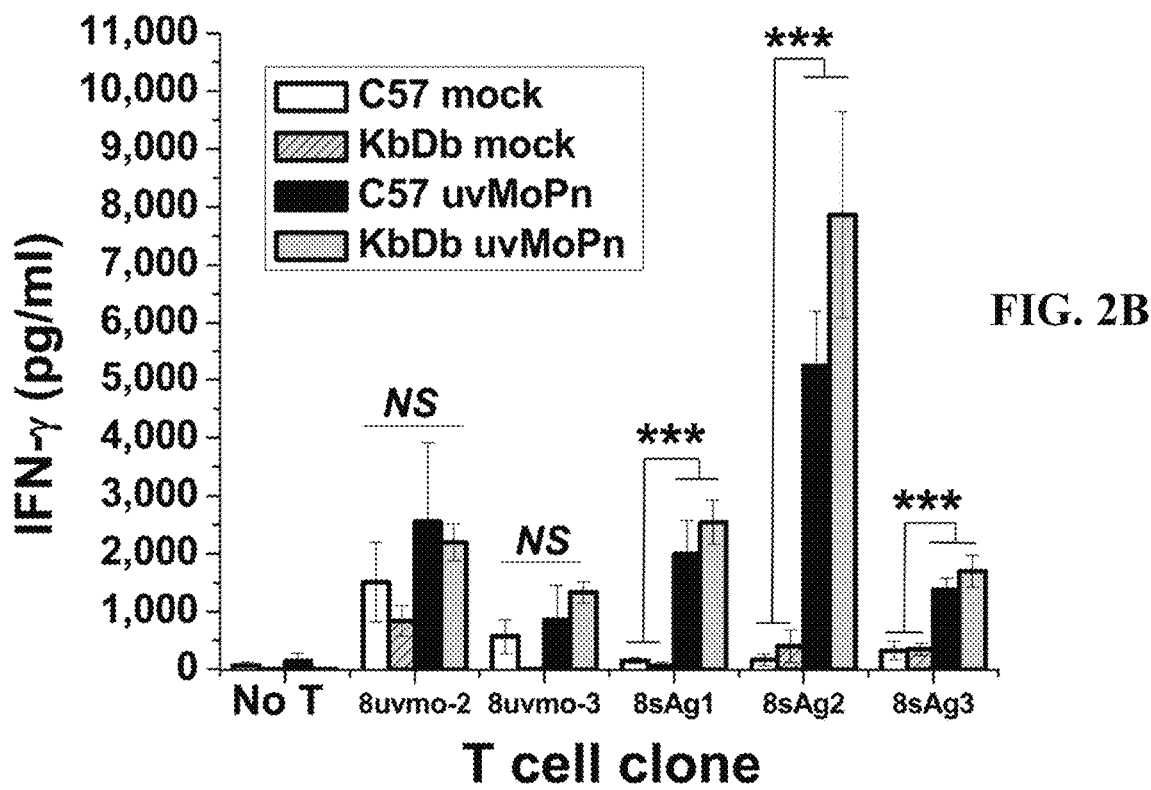
Figure 3A:
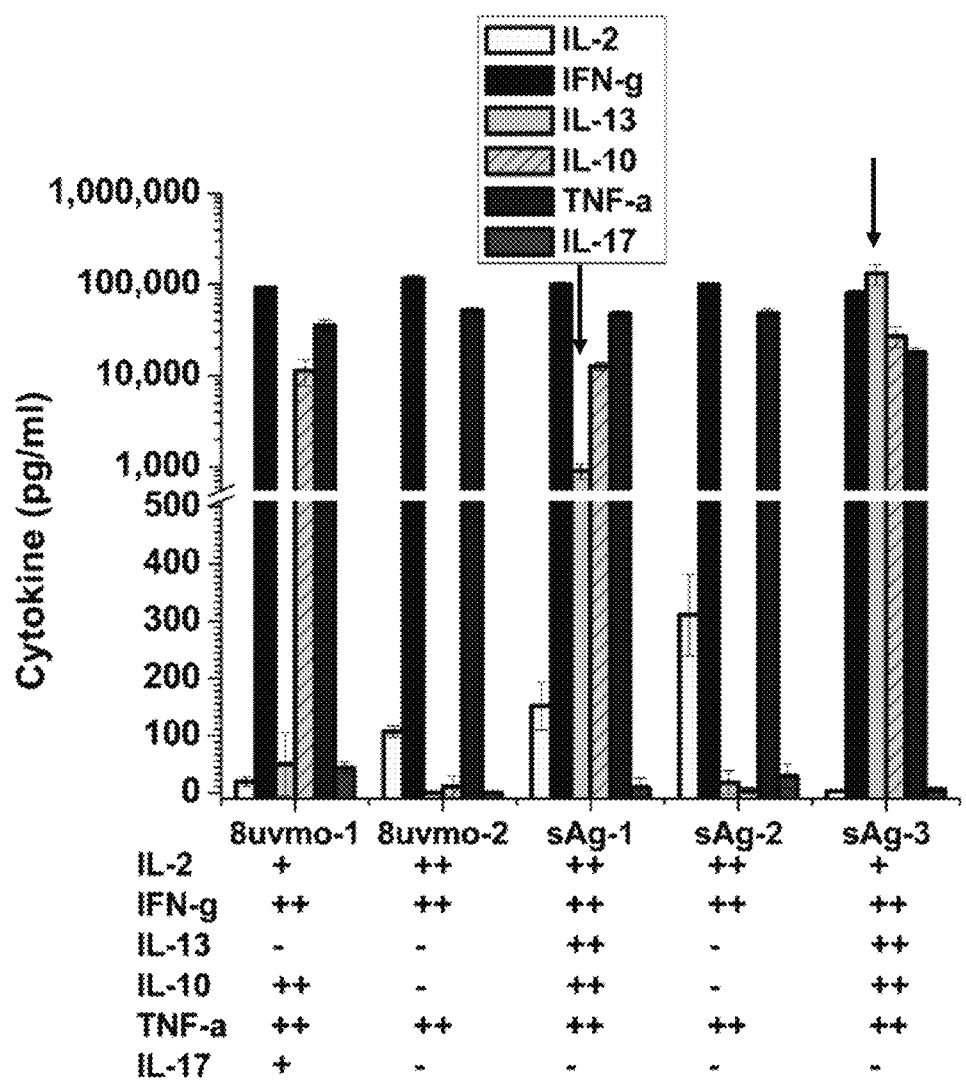

FIG. 2B shows graphical data representative IFN-γ levels in CD8 T cell clones as determined by ELISA and represents mapping of MHC restriction elements using naïve splenocytes augmented by IL-7. CD8 T cell clones were mock-activated and uvMoPn-activated with irradiated (1000 rad) naïve C57BL/6 and KbDb knockout mouse splenocyte APC. Supernatants were collected at 72 h and levels of IFN-γ determined by ELISA. Data presented are aggregate data from two independent experiments. *=p value <0.05: =p value <0.005: *=p value <0.0005. Conclusion: Three of the five CD8 T cell clones (8sAg-1, -2, -3) were activated as well or better by Balb/c and class Ia-deficient naïve splenocytes pulsed with uvMoPn as by syngeneic naïve C57BL/6 pulsed with uvMoPN, consistent with not being conventionally-restricted by MHC class Ia molecules;

FIG. 3A shows cytokine patterns in CD8IL-13 T cell clones. The CD8IL-13 T cell clones were activated with immobilized anti-CD3 antibody. Supernatants were collected at 24 h and indicated cytokine patterns determined by ELISA. Aggregate data from two independent experiments shown. All CD8 clones produced IL-2, large amounts of IFN-γ and TNF-α, most produced large amounts of IL-10, and two produced large amounts of IL-13 (sAg-1 and sAg-3); sAg-1 and sAg-3 (also known respectively as 8sAg1, 8sAg3) are the first antigen-specific CD8IL-13 T cell clones ever published; arrows highlight IL-13 bars.

Figure 3B:
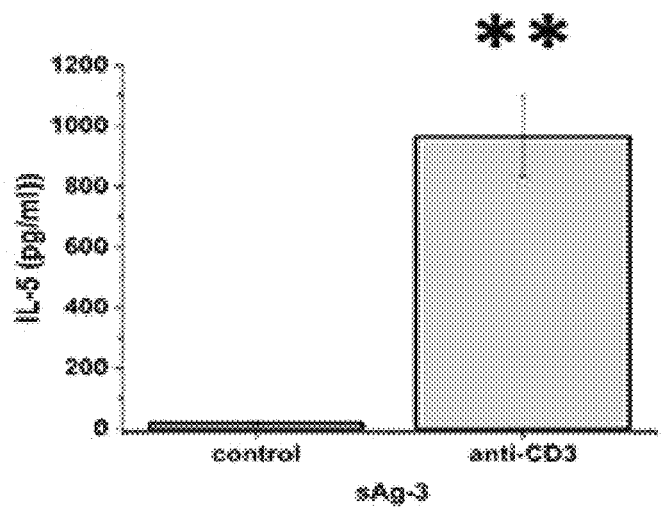
Figure 4:
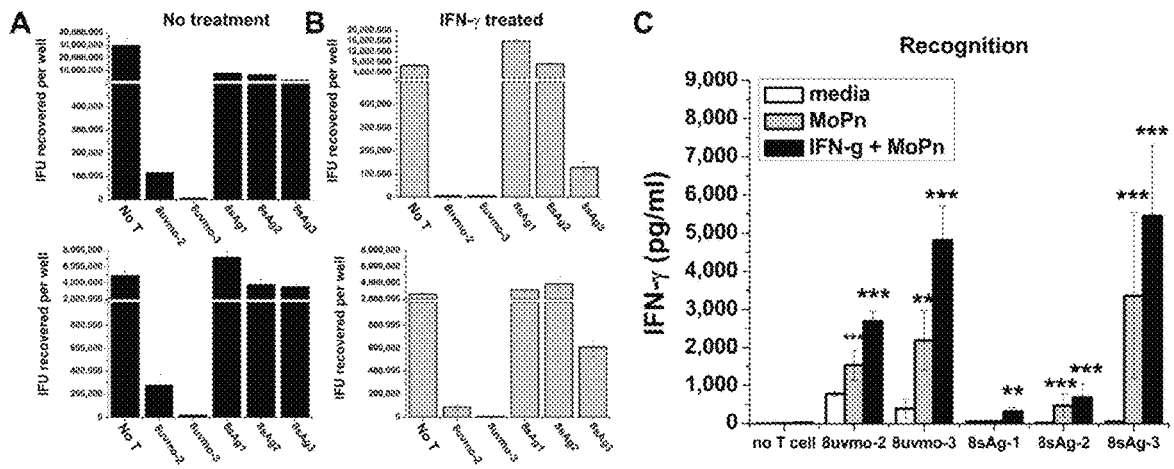
Figure 5:
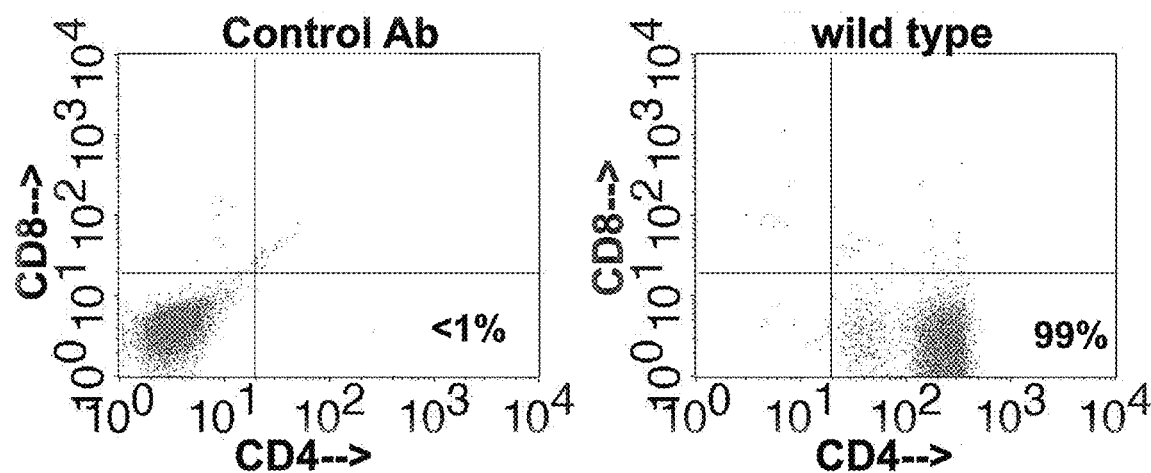

FIG. 3B shows IL-5 production by CD8IL-13 T cell clone sAg-3 and confirms murine micro array data in Table 1 that shows activated CD8IL-13 T cell clone sAg-3 produces IL-5 when activated (**=p value <0.01);

FIG. 4 shows graphical data representative of CD8 T cell clones' ability to terminate *C. muridarum* replication in upper reproductive tract epithelial cells. C57epi.1 cells, untreated or pretreated with IFN-γ (10 ng/ml for 10 h), were infected with 3 IFU *C. muridarum* per cell. 4 h later the inocula were removed, monolayers washed; then T cells were added. Wells were harvested 32h post-infection and recovered IFU quantified on McCoy monolayers. Top panels of subpart A and subpart B of FIG. 4=quantified data from experiment #1: bottom panels of subpart A and subpart B of FIG. 4=quantified data from experiment #2. Subpart C of FIG. 4) Supernatants in experiments #1 and #2 (shown in subparts A and B of FIG. 4) were collected immediately prior to harvesting monolayers; IFN-γ levels were determined by ELISA, which are graphically shown in subpart C of FIG. 4. Aggregate data from experiments #1 and #2. *=p value <0.05: =p value <0.005; *=p value <0.0005. Conclusion: All CD8 T cell clones recognized infected epithelial cells, with variable ability to terminate *Chlamydia* replication; and FIG. 5 shows graphical data representative of the amount of CD4 T cells present versus the amount of CD8 T cells present within a Control Ab (left graph) and within wild type (right graph), the data supporting that conventional T cell culture methodologies based on irradiated naïve antigen-presenting cells (splenocytes) pulsed with UV-inactivated

Figure 8:
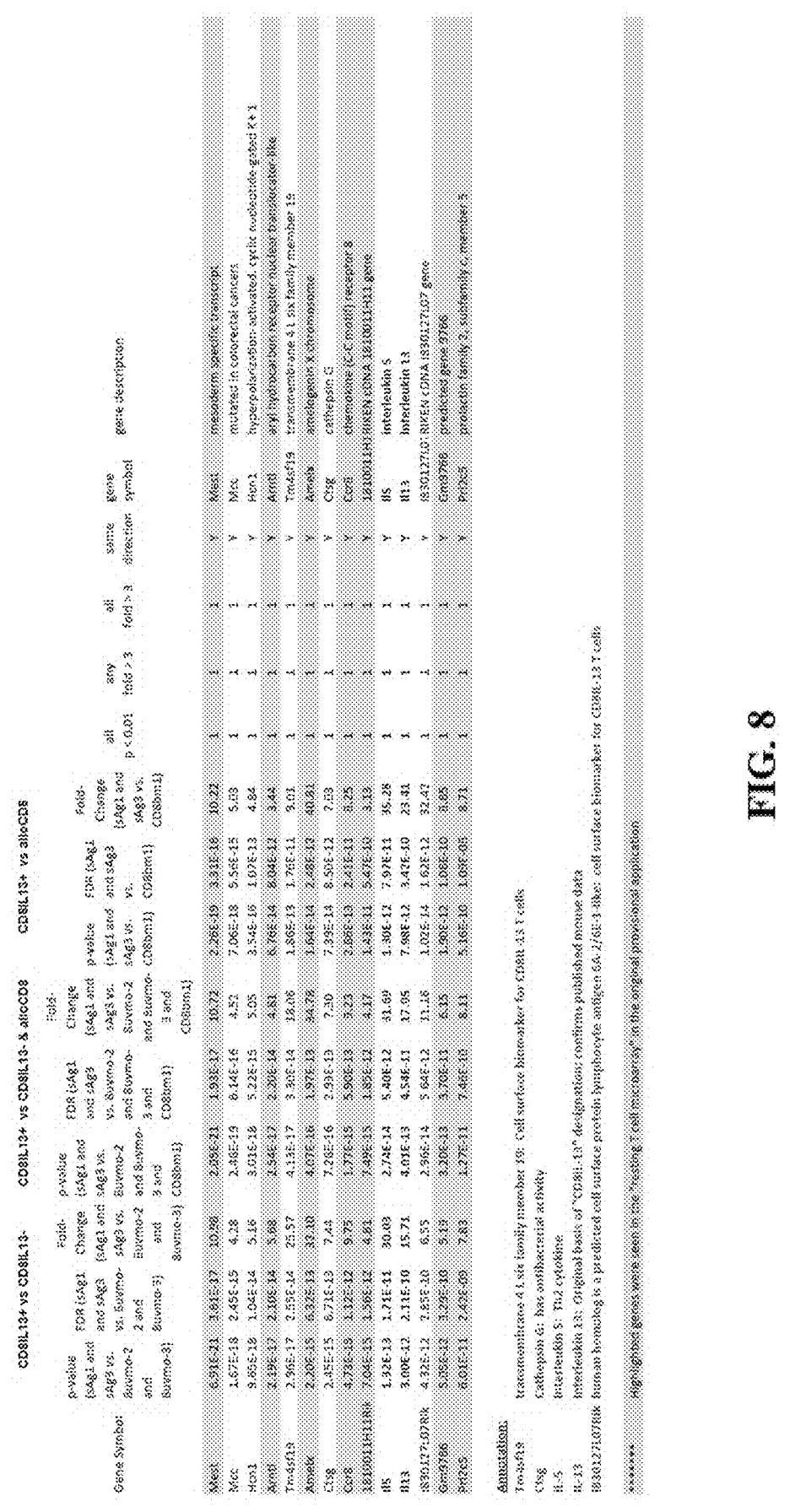
Figure 9:
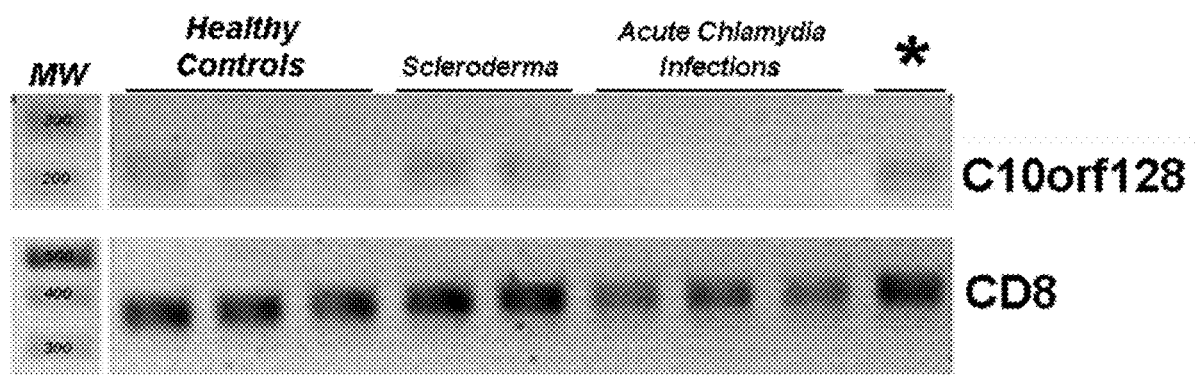
Figure 10:
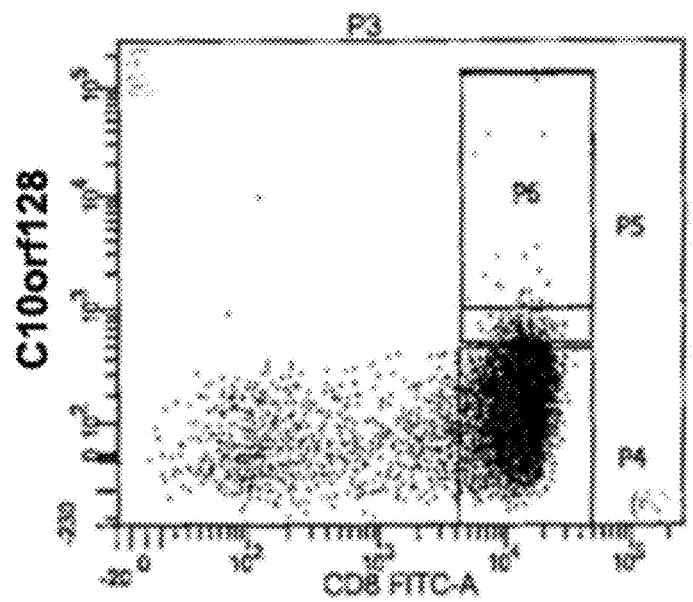
Figure 11B:
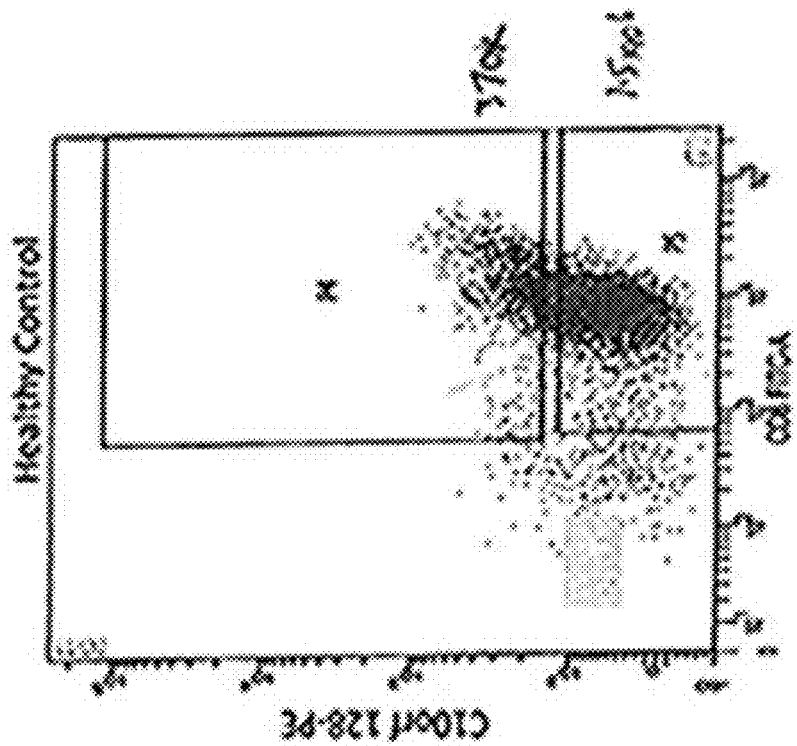
Figure 11A:
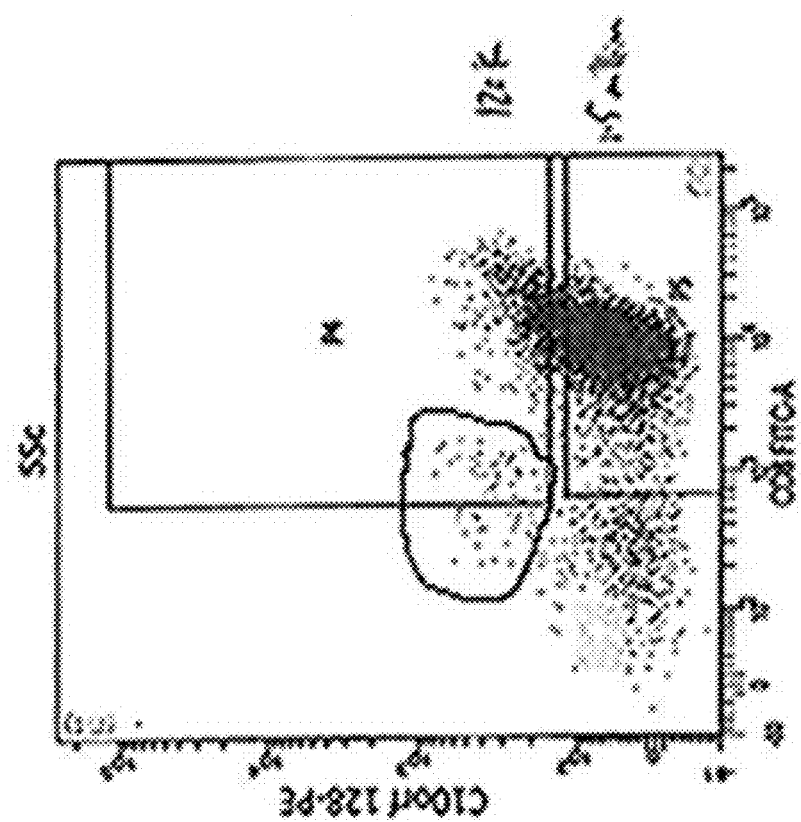
Figure 12:
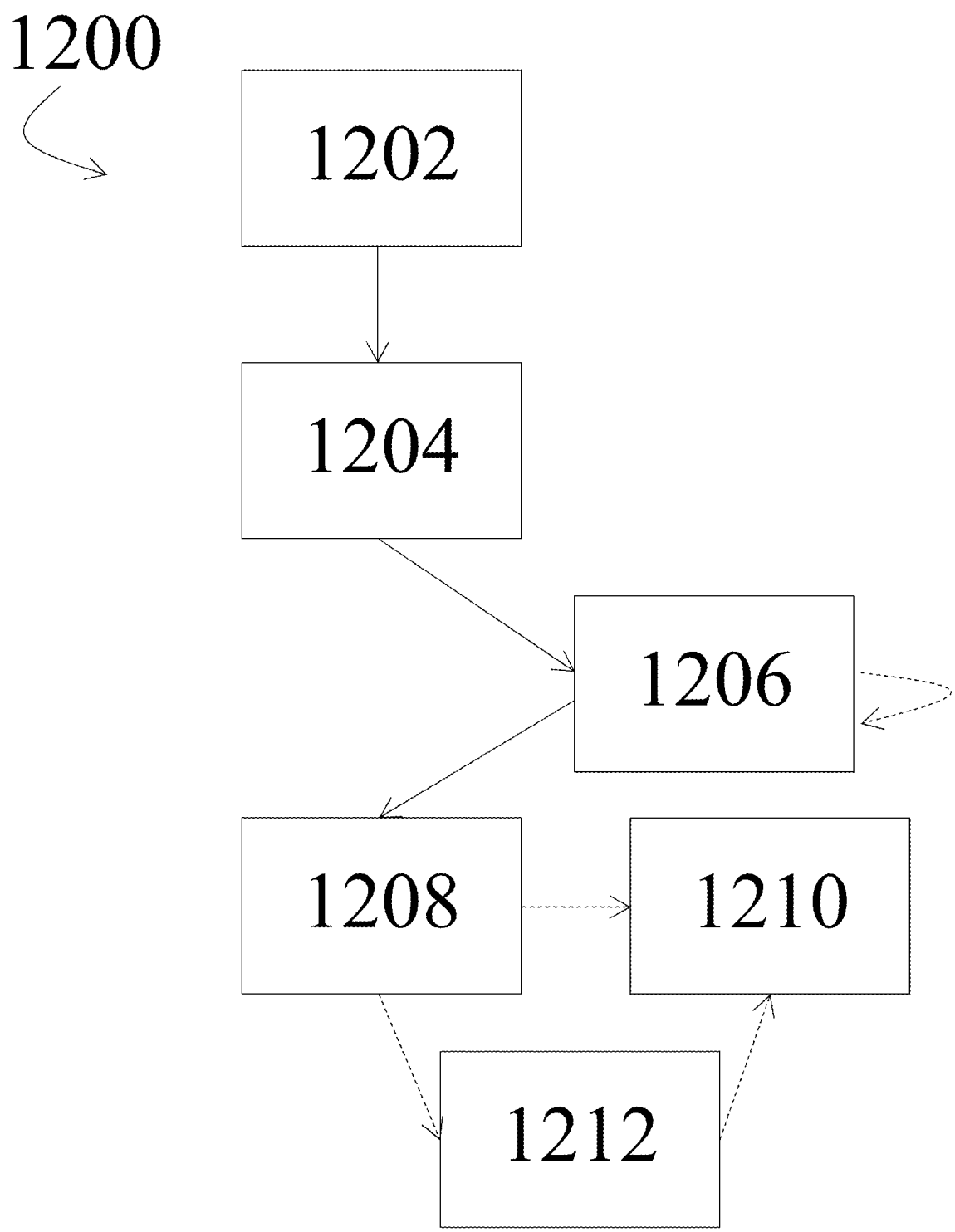
Figure 13:
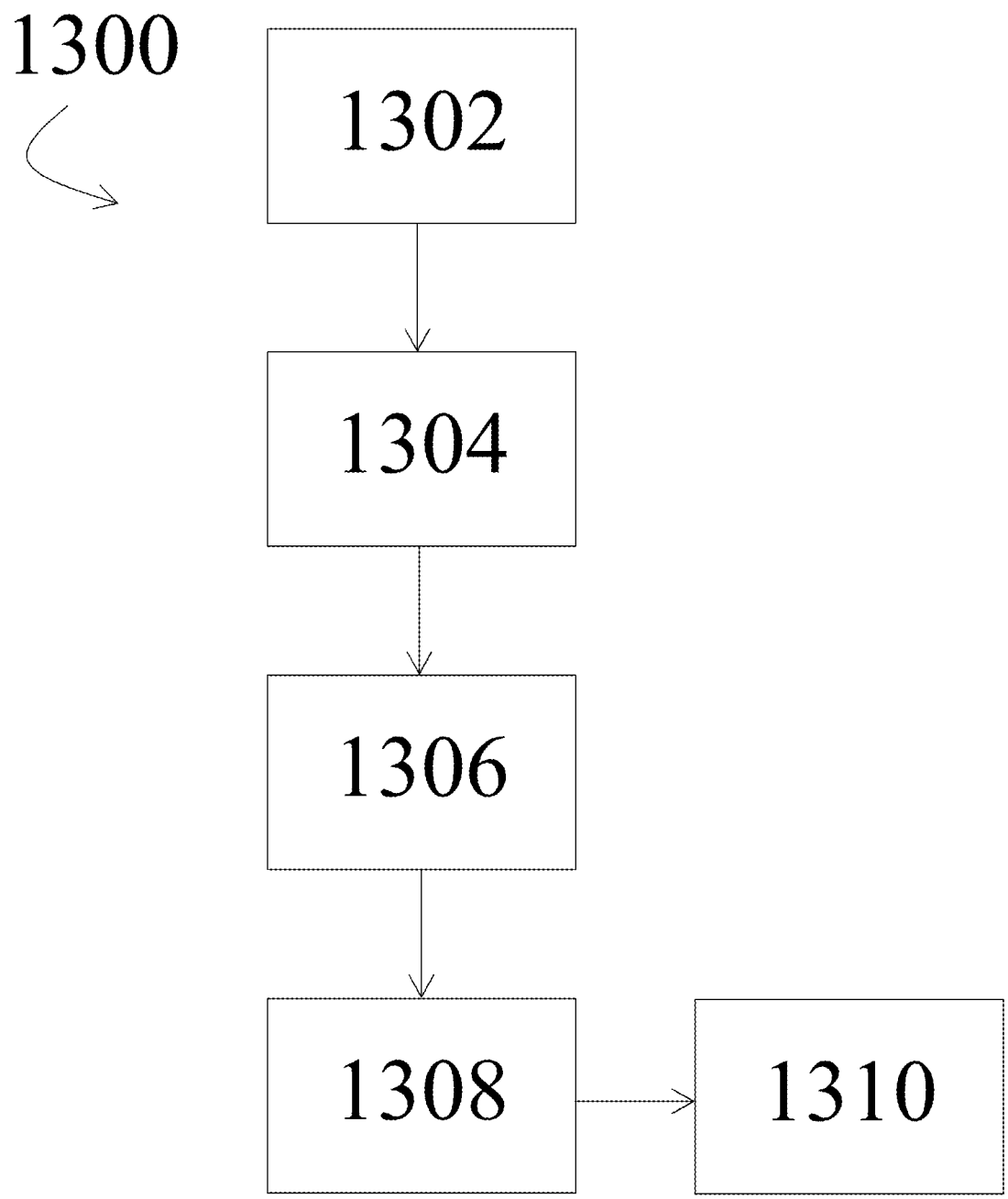
Figure 14:
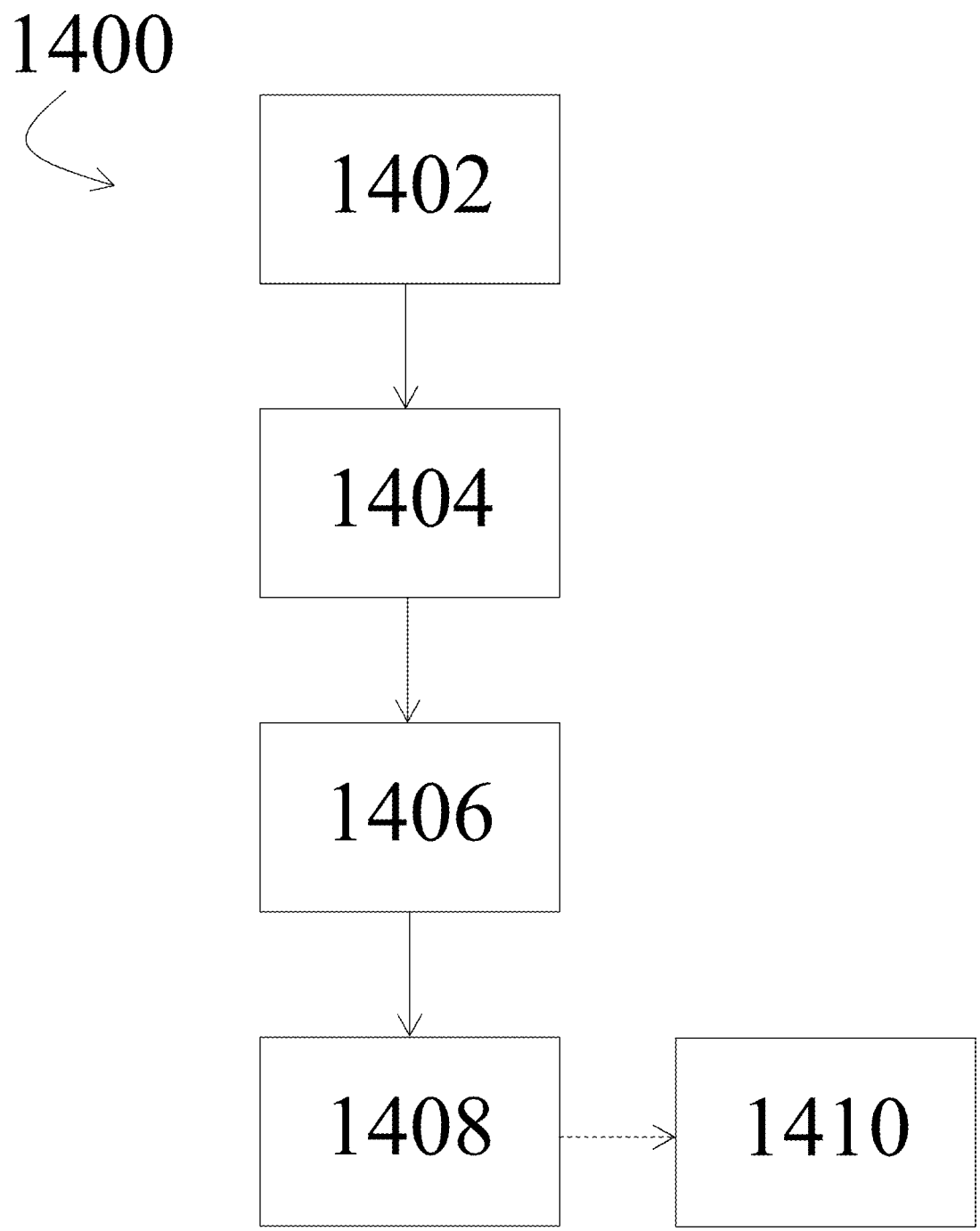
Figure 15:
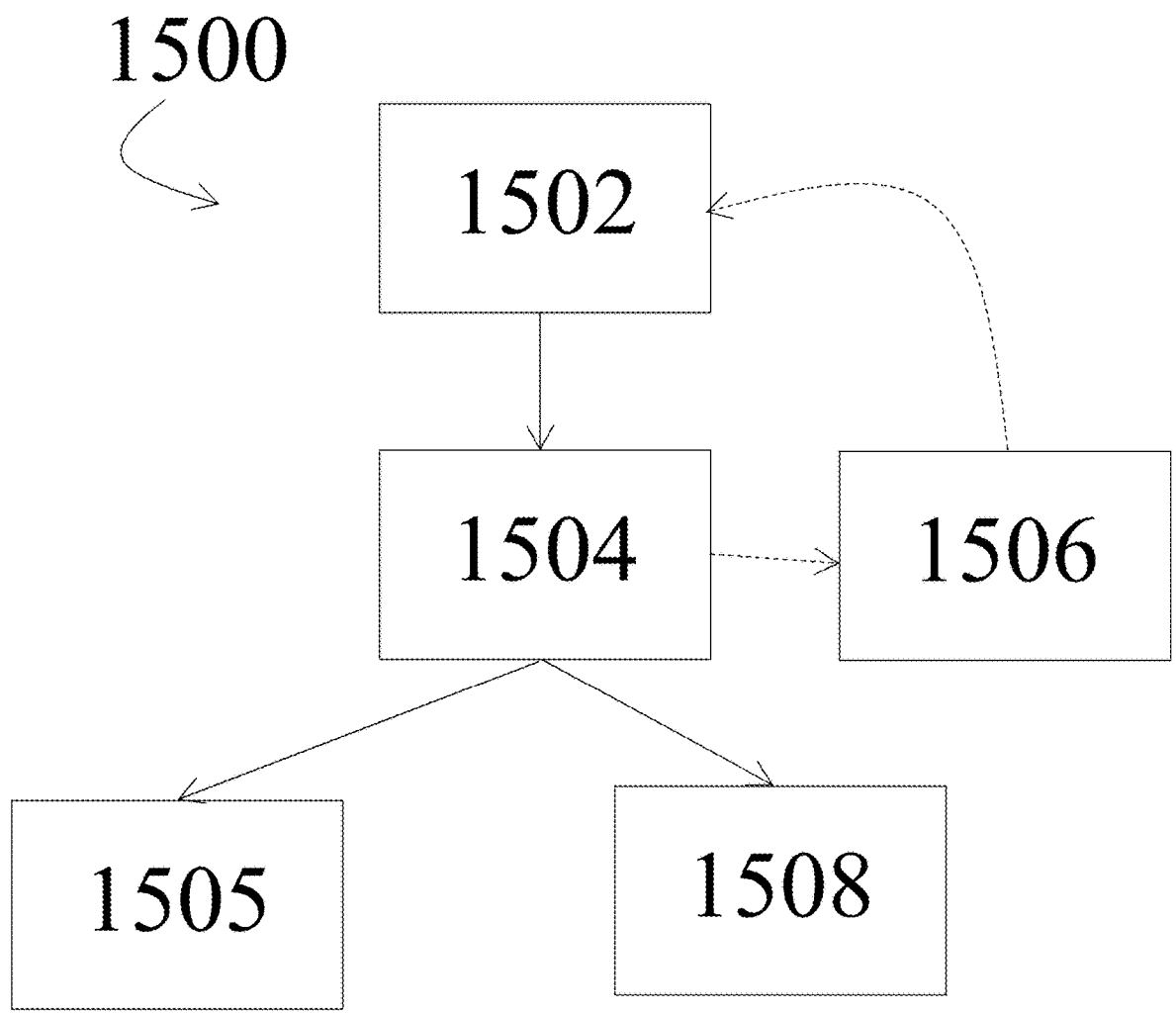

*Chlamydia* select out only CD4 T cells in vitro, and therefore are not useful for isolating *Chlamydia*-specific CD8 T cells; and FIG. 6 shows a chart that lists biomarkers for unactivated mouse CD8IL-13 T cells. T cell clones at the end of their culture cycle were cultured for 3 additional days in medium supplemented with recombinant mouse IL-7 (3 ng/ml): total RNA was harvested from conventional CD8 T cell clones (8uvmo-2, 8uvmo-3, and a alloreactive CD8 T cells clone designated CD8bm1) and CD8IL-13 T cell clones 8sAg-1 and 8sAg-3 for comparison. Experiment was repeated three times for CD8IL-13 T cell clones 8sAg-1 & 8sAg-3: four times for the controls (8uvmo-2, 8uvmo-3, CD8bm1). Gene expression patterns were compared using the Affymetrix Mouse Gene 1.0 ST microarray: "same direction" refers to fold-changes being positive for all comparisons, "sig" refers to fold-change differences having p values <0.001, ">3" refers to fold-change for comparisons being >3-fold; genes unique to CD8IL-13 T cell clones score Y/1/1 in the table, and FIG. 7 a chart that lists biomarkers unique to the CD8IL-13 T cell clones 8sAg-1 and 8sAg-3 with gene annotation; and FIG. 8 shows a chart that lists biomarkers for activated mouse CD8IL-13 T cells. CD8 T cell clones at the end of their culture cycle were activated overnight with immobilized anti-CD3 antibody in usual medium: 14 h later total RNA was harvested from the conventional CD8 T cell clones (8uvmo-2, 8uvmo-3, and an alloreactive CD8 T cells clone designated CD8bm1) and CD8IL-13 T cell clones 8sAg-1 and 8sAg-3 for comparison. Experiment was repeated four times for each clone. Gene expression patterns were compared using the Affymetrix Mouse Gene 1.0 ST microarray. Genes designated activated CD8IL-13 biomarkers had to be enhanced at least 3-fold with p values <0.01 for all three comparisons; *Chlamydia*-specific CD8 CD8IL-13+ vs *Chlamydia*-specific CD8 CD8IL-13−, CD8IL-13+ vs all others, and CD8IL-13+ vs, the alloreactive CD8 T cell clone CD8bm1;

FIG. 9 shows semi-quantitative evaluation of C10orf128 mRNA levels in CD8 T cells purified from the peripheral blood of human subjects. Perhaps more specifically, FIG. 9 shows inverted images of products of such RT-PCR reactions separated on 2.5% agarose gels containing ethidium bromide. Four groups of human subjects were recruited: healthy controls: scleroderma; acute *Chlamydia* infection: necrotizing lymphadenitis of unknown etiology. Total RNA was isolated from the purified CD8 T cell pools and subjected to RT-PCR with primers for C10orf128 (human homolog of mouse CD8IL-13 biomarker 1810011H11Rik) and CD8 (loading control). Patients with scleroderma had equal to or greater C10orf128 mRNA in their circulating CD8 T cell pool than all other subjects in spite of treatment with mycophenolate (a therapeutic toxin affecting activated lymphocytes);

FIG. 10 shows graphical data related to a circulating CD8 T cell pool (top graph) and a value interpretation relating to the same (bottom chart), which supports that C10orf128 positive CD8 T cells ("C10orf128pos") are ~0.2% of the circulating CD8 T cell pool in a healthy individual (gate P6). Conclusion: There are sufficient C10orf128pos T cells circulating in the peripheral blood of a healthy person to do practicable isolation for functional and molecular studies. Extrapolating from the results shown in FIG. 9, there should also be sufficient C10orf128pos CD8 T cells in the peripheral blood of individuals with systemic sclerosis to do practicable isolation of C10orf128pos CD8 T cells for functional and molecular studies;

FIGS. 11A and 11B show the summary of Aria II flow cytometer sorting data from CD8 T cells from a scleroderma subject (FIG. 11A) and a healthy control subject (FIG. 11B) into C10orf128 positive (gate P4) and negative (gate P5) pools using commercially available anti-CD8 antibody and our custom rabbit anti-C10orf128 antiserum: the C10orf128 positive CD8 T cells unique to the scleroderma subject versus the healthy control are circled: the majority of the C10orf128 positive CD8 T cells (CD8IL-13 T cells) are in sorting gate P4. Genes uniquely expressed in P4 gate of the scleroderma subject, determined by subtraction methodology, include IL-13 and IL-5, consistent with the mouse CD8IL-13 T cell data presented in FIG. 3A, and confirming that the CD8lowC10orf728positive CD8 T cells in gate P4 of the scleroderma subject (circled in FIG. 11A) are human CD8IL-13 T cells viably sorted from conventional CD8 T cells using anti-CD8 antibody plus our custom C10orf128-specific antiserum;

FIG. 12 shows a flow chart representative of an exemplary method for the production of a C10orf128-specific antisera of the present disclosure;

FIG. 13 shows a flow chart of an exemplary method of diagnosing a condition mediated by CD8IL-13 producing cells of the present disclosure;

FIG. 14 shows a flow chart of an exemplary method of diagnosing a medical condition by measuring an expression level of Clc (galectin 10 protein); and FIG. 15 shows a flow chart of an exemplary method of analyzing small molecule efficacy in disrupting CD8IL-13 pathophysiology.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

DETAILED DESCRIPTION

For the purposes of promoting an understanding of the principles of the present disclosure, reference will now be made to the embodiments illustrated in the drawings and specific language will be used to describe the same. It will nevertheless be understood that no limitation of scope is intended by the description of these embodiments. On the contrary, many modifications and other embodiments of the technology described herein will come to mind to one of skill in the art to which the present disclosure pertains having the benefit of the teachings presented in the present descriptions and associated figures. Therefore, it is understood that this disclosure covers any such alternatives, modifications, and equivalents as may be included within the spirit and scope of this application as defined by the specification and appended claims. As previously noted, while this technology may be illustrated and described in one or more preferred embodiments, the compositions, systems, and methods hereof may comprise many different configurations, forms, materials, and accessories.

In the following description, numerous specific details are set forth in order to provide a thorough understanding of the present disclosure. Particular examples may be implemented without some or all of these specific details and it is to be understood that this disclosure is not limited to particular biological systems, which can, of course, vary.

Furthermore, wherever feasible and convenient, like reference numerals are used in the figures and the description to refer to the same or like parts or steps. The drawings are in a simplified form and not to precise scale. It is understood that the disclosure is presented in this manner merely for explanatory purposes and the principles and embodiments described herein may be applied to devices and/or system components that have dimensions/configurations other than as specifically described herein. Indeed, it is expressly contemplated that the size and shapes of the composition and system components of the present disclosure may be tailored in furtherance of the desired application thereof.

Unless defined otherwise, all technical and scientific terms used herein have the same meaning as commonly understood by one of skill in the relevant arts. Although any methods and materials similar to or equivalent to those described herein can be used in the practice or testing of the subject of the present application, the preferred methods and materials are described herein. Additionally, as used in this specification and the appended claims, the singular forms "a", "an" and "the" include plural referents unless the content clearly dictates otherwise. Furthermore, unless specifically stated otherwise, the term "about" refers to a range of values plus or minus 10% for percentages and plus or minus 1.0 unit for unit values, for example, about 1.0 refers to a range of values from 0.9 to 1.1.

As used herein, the term "therapeutically effective dose" means (unless specifically stated otherwise) a quantity of a compound which, when administered either one time or over the course of a treatment cycle affects the health, wellbeing or mortality of a subject (e.g., and without limitation, delays the onset of and/or reduces the severity of one or more of the symptoms associated with an active inflammatory disease or condition). The amount of the disclosed compound to be administered to a recipient will depend on the type of disease being treated, how advanced the disease pathology is, and the characteristics of the patient or subject (such as general health, age, sex, body weight, and tolerance to drugs).

A "subject" or "patient," as used herein, is a mammal, preferably a human, but can also be an animal.

A "marker" or "biomarker" as the terms are used herein may be described as being differentially expressed when the level of expression in a subject who is experiencing an active disease state is significantly different from that of a subject or sample taken from a healthy subject. A differentially expressed marker may be overexpressed or underexpressed as compared to the expression level of a normal or control sample or subjects' baseline. The increase or decrease, or quantification of the markers in a biological sample may be determined by any of the several methods known in the art for measuring the presence and/or relative abundance of a gene product or transcript. The level of markers may be determined as an absolute value, or relative to a baseline value, and the level of the subject's markers compared to a cutoff index. Alternatively, the relative abundance of the marker or markers may be determined relative to a control, which may be a clinically normal subject.

A "profile" or "assay" is a set of one or more markers and their presence, absence, and/or relative level or abundance (relative to one or more controls). For example, a cytokine profile is a dataset of the presence, absence, relative level or abundance of cytokines present within a sample. A genomic or nucleic acid profile is a dataset of the presence, absence, relative level or abundance of expressed nucleic acids (e.g., transcripts, mRNA, or the like). A profile may alternatively be referred to as an expression profile.

"Down-regulation" or "down-regulated" may be used interchangeably and refer to a decrease in the level of a marker, such as a gene, nucleic acid, metabolite, transcript, protein, or polypeptide. "Up-regulation" or "up-regulated" may also be used interchangeably and refer to an increase in the level of a marker, such as a gene, nucleic acid, metabolite, transcript, protein, or polypeptide. Also, a pathway, such as a signal transduction or metabolic pathway may be up- or down-regulated.

Of significance of the present disclosure, at least in part, is not the particular methods used to detect the marker or set of markers, but what the markers are used to detect. As previously noted, there are many methods that may be used to detect the expression, quantification, or profile of one or more biomarkers. Once the marker or set of markers to be detected or quantified is identified, any of several techniques (that are now know n or hereinafter developed) may be used, with the provision of appropriate reagents. One of skill in the art, when provided with the one or more biomarkers to be identified, will be capable of selecting the appropriate assay (e.g., a PCR-based or a microassay-based assay for nucleic acid markers, an ELISA, protein or antibody microarray or similar immunologic assay, etc.) for performing the methods disclosed herein.

Methods of producing antisera and antibodies for use in protein or antibody arrays, or other immunology based assays are known in the art. Once the marker or markers are identified, one of skill in the art will be able to use such information to prepare one or more appropriate antibodies and antisera and perform the selected assay. For preparation of monoclonal antibodies directed towards a biomarker, any technique that provides for the production of antibody molecules by continuous cell lines in culture may be used. For example, but without limitation, human antibodies may be used and can be obtained by transforming human B cells with EBV virus in vitro, using a hybridoma technique, or as is otherwise known in the art. Likewise, polyclonal antibodies (or a fragment thereof) can be raised according to known methods by administering the appropriate antigen or epitope to a host animal (e.g., a pig, cow, horse, rabbit, goat, sheep, mice, etc.). Antibodies useful in practicing the present disclosure may be polyclonal or monoclonal antibodies unless specifically described as one or the other herein.

The compounds described herein, and the pharmaceutically acceptable salts thereof, can be used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the ranges described herein. For oral administration, the disclosed compounds or salts thereof can be combined with a suitable solid or liquid carrier or diluent to form capsules, tablets, pills, powders, syrups, solutions, suspensions and the like. Tablets, pills, capsules, and the like contain from about 1 to about 99 weight percent of the active ingredient and a binder, excipients, a disintegrating agent, a lubricant, and/or a sweetening agent (as are known in the art).

The term "lymphocyte" means a nucleated or "white" blood cell (leukocyte). Lymphocytes include T-cells, B-cells, and the like, and other immune regulatory cells.

A "T-cell" or "T cell" is a class of lymphocyte responsible for cell-mediated immunity and for stimulating B-cells. A stimulated B-cell produces antibodies for specific antigens. Both T-cells and B-cells function to recognize non-self antigens in a subject. Non-self-antigens include those of viruses, bacteria, and other infectious agents. T-cell based immune response can occur either directly, by cross reaction with allogeneic major histocompatibility complex (MHC) molecules, or indirectly (by reaction with allogeneic peptide fragments bound to host MHC molecules on antigen-presenting cells or allogeneic target cells). T-cells not only initiate the immune response, but also mediate antigen-specific effector responses. In addition. T-cells secret soluble factors to regulate the activity of other leukocytes. For example, activated T-helper cells produce interleukins, gamma interferon, and leukotrienes.

Embodiments of the present disclosure provide for various compositions and techniques that relate to and/or leverage isolated *Chlamydia*-specific CD8+ T cells that express interleukin-13 (IL-13) and various methods of isolating the same. Specifically, certain embodiments of the CD8+ T cells and methods disclosed herein provide useful insights into *Chlamydia*-associated immunopathology and the pathogenesis of human inflammatory/rheumatologic disease states such as systemic sclerosis.

Additionally, novel human biomarkers C10orf128 (the human homolog of mouse 1810011H11Rik), IL-13, IL-5, Arntl, Cep85L, and Amelx, as well as a related CD8IL-13 cell surface domain peptide for C10orf128 (SEQ ID No. 1) are disclosed. The biomarkers described herein may be used to identify and/or purify a subset of IL-13 and/or IL-5 expressing CD8 T cells that are unique to patients experiencing an active inflammatory disease state.

For example, in at least one of the investigations described in the present disclosure. *Chlamydia*-specific CD8IL-13 T cell clones were isolated from mice that self-cleared genital tract infections (that were associated with significant genital tract scarring similar to the human infection) using the novel methodologies described herein. Scarring is the biologic trait shared between *Chlamydia* infections and scleroderma, two inflammatory disease states. The unique molecular finger print of the resulting CD8IL-13 T cell clones was determined by comparative gene expression micro array analysis and a putative 95 amino acid transmembrane protein called 1810011H11Rik was identified. Heretofore 1810011H11Rik was entirely uncharacterized, as was its highly conserved human homolog C10orf128. Accordingly, the murine-proven novel methodologies described herein allowed for the determination of multiple human biomarkers of significant importance in connection with the diagnosis and treatment of several disease conditions.

Importantly, human peripheral blood CD8 T cells, including those taken from scleroderma patients, was found to contain mRNA for C10orf128. Furthermore, it was determined that those patients experiencing an active inflammatory disease (such as scleroderma, for example) exhibited elevated levels of C10orf128 mRNA in their CD8 T cell pool. As described in further detail below, at least one application of this finding is that purified CD8 T cells taken from a patient's peripheral blood can be analyzed for C10orf728 expression (via gene expression microarray analysis, RT-PCR, flow cytometry or otherwise) for diagnostic and therapeutic purposes. Leveraging these important findings, in at least one exemplary embodiment of the present disclosure, a diagnostic method for identifying the presence of an active inflammatory disease state in a human patient is provided. There, such method may comprise the steps of purifying a population of CD8 T cells collected from peripheral blood of a human subject; isolating RNA from the purified population of CD8 T cells: and quantifying a level of expression of the C10orf128, IL-13, IL-5, Arntl, Cep85L, or Amelx biomarker expression in the isolated RNA.

In at least one embodiment, any expression of identifying an elevated level of the C10orf128, IL-13, IL-5, Arntl, Cep85L, Amelx, Clc, or Alox5 biomarker greater than or equal to 1.5 times a level established in healthy individuals may be considered indicative of the subject experiencing an active condition mediated by a subset of CD8 T cells that are polarized to produce IL-13 and/or IL-5 in a patient's peripheral blood. In another embodiment, the same practical outcome is achieved using flow cytometry to gate on CD8 T cells, then quantify levels of C10orf128, IL-13, IL-5, Arntl, Cep85L, Amelx, Clc, and/or Alox5 biomarker. There, in at least one embodiment, any expression of one or more of the aforementioned biomarkers greater than or equal to 1.5 times a level established in healthy individuals may be considered indicative of the subject experiencing an active condition mediated by a subset of CD8 T cells that are polarized to produce IL-13 and/or IL-5 in a patient's peripheral blood.

With respect to purifying the population of CD8 T cells and, perhaps more specifically. CD8IL-13 T cells and/or CD8IL13/5 T cells, the present disclosure also provides novel antisera and antibody compositions and methodologies for making the same. In at least one embodiment, such an antibody and/or antiserum composition may be used to sort/purify C10orf128 positive CD8 T cells from a subject's blood (i.e. an antiserum to the putative extracellular domain of C10orf128).

Additionally or alternatively, the novel compositions and methodologies hereof may be formulated and used to target CD8IL13/5 T cells (e.g., using anti-C10orf128 biologics) for the purpose of ameliorating disease manifestations. Such aspects of the present disclosure are noteworthy as the methodologies and techniques described herein represent significant advances over the conventional diagnostic and therapeutic interventions currently available in connection with subjects experiencing an active inflammatory disease state and, in particular, scleroderma and *Chlamydia*.

The inventive concepts of the present disclosure, as well as the underlying methods and techniques used in determining the same, will now be described generally to promote conceptual understanding. Such general description is then followed by a more in-depth analysis of the related experimental methodologies and results.

It is important to understand the nature of *Chlamydia*-specific CD8 T cell responses because that CD8 T cell response has been associated with immunopathology and is representative of a natural mucosal immune response that is poorly understood and extremely difficult to study in humans. In general, CD4 and CD8 T cell subsets have a role in protection and immunopathology during *Chlamydia* genital tract infections; however, less is known about the role of CD8 T cell subsets than CD4 T cell subsets during *Chlamydia* genital tract infections and other disease states. To address this, *Chlamydia*-specific CD8 T cell clones were isolated from mice that had previously cleared *Chlamydia muridarum* (*C. muridarum*) genital tract infections and their immunobiology investigated, including restriction elements, cytokine patterns and the ability to terminate *Chlamydia* replication in upper reproductive tract epithelial cells.

As described in more detail below in the "Materials and Methods" section, the *Chlamydia*-specific CD8 T cells clones described herein are a minority subset in polyclonal T cell populations that were expanded in vitro from C57BL/6 mice that previously cleared *C. muridarum* genital tract infections. To further advance the study of *Chlamydia* pathogenesis, the inventor of the present disclosure developed novel methodologies for isolating and studying antigen-specific CD8 T cells (methods and materials described in further detail in Johnson R M, Kerr M S, Slaven J E. *An atypical CD8 T-cell response to Chlamydia muridarum genital tract infections includes T cells that produce interleukin-13*, Immunology 2014; 142(2): 248-57 (the "Johnson Publication"), which is hereby incorporated by reference herein in its entirety).

Due to the novel methodologies described herein and/or in the Johnson Publication, it has been determined that the insights provided by the *C. muridarum* mouse model of the present disclosure can be applied to human diagnostics and therapeutic interventions. Indeed, the identified biomarkers have a wide range of application in human diagnostics and medicine.

Materials and Methods

While others have demonstrated a role for CD8 T cells in clearing the genital tract in the *C. muridarum* mouse model, those CD8 T cell lines and CD8 T cell clones were isolated after intravenous injection of 100 million live infectious *Chlamydia* units (IFU), with an intravenous booster of inclusion-forming units and subsequent continuous culture using UV-inactivated *C. muridarum* and irradiated-naïve splenocytes. This is distinct from the methodology employed herein, which is based on natural vaginal infection (50,000 IFU inoculated one time) and continuous culture ex vivo with irradiated-immune splenocytes that yields significantly different results. Indeed, the inventor's methodologies induce a mucosal immune response (as opposed to the systemic immune response seen in response to conventional techniques—intravenous injection). Unlike the systemic immune system that responds to antigens in the blood, the mucosal immune system is juxtaposed to the mucosal surfaces in direct contact with the external antigenic environment (i.e. the mucosal surfaces of the respiratory, gastrointestinal, and urogenital tracts, for example) and T cells resulting from mucosal immune responses have mucosa-specific regulatory and effector characteristics. Indeed, conventional culture systems do not yield a CD8IL-13 T cell line nor clone and are incapable of doing so. However, CD8 T cells and T cell clones resulting from the presently disclosed methodology naturally express IL-13. Furthermore, in parallel and consistent with the inventor's CD8IL-13 mouse data, human studies by other investigators based on *Chlamydia*-specific CD8 T cell clones isolated from infected individuals showed that the majority of the CD8 T cell clones were not restricted by MHC class Ia molecules without investigation of IL-13 or IL-5.

The novel materials and methods developed to clone antigen-specific T cells (e.g., CD8IL-13 and/or CD8IL-13/5) will now be described in additional detail. As noted above, conventional T cell culture conditions based on inactivated *Chlamydia muridarum* and continuous passage with irradiated naive splenocytes yields only *Chlamydia*-specific CD4 T cells (see FIG. 5). For that reason, to study CD8 T cells, an alternative culture system was developed based on soluble antigen and immune Ig-receptor-bearing antigen presenting cells (APC) capable of utilizing cross-presentation pathways to generate more CD8 T cell epitopes and promote greater expansion of CD8 T cells (Subpart A of FIG. 1).

Mice 4-5 week old female C57BL/6 mice from Harlan Labs (Indianapolis, Ind.) and $K^bD^b$ double knockout female mice (lack MHC class Ia molecules) from Taconic (Hudson, N.Y.) were used. All mice were housed in a pathogen-free barrier animal facility.

Epithelial Cells and Bacteria.

C57epi.1 epithelial cells and McCoy fibroblasts were cultured. *Mycoplasma*-free *Chlamydia muridarum* (Nigg), previously known as *C. trachomatis* strain mouse pneumonitis (MoPn) (Nigg) was grown in McCoy cells. Elementary body (EB)-depleted *Chlamydia* antigen was prepared by infecting 175 $cm^2$ flasks of McCoy cells with *C. muridarum* at 3 IFU per cell. 32 h post infection the monolayers were removed using sterile glass beads, sonicated 60 sec. spun at low speed (464 g×10 min) to remove debris, then centrifuged 19.000 g×30 min to pellet elementary bodies (EB); ~99.998% depletion. EB-depleted supernatants were collected, concentrated (4000 g×30 min) in ultrafiltration centrifuge units with 30 kd MW cut off (Amicon Ultra-15; Millipore, Billerica Mass.), aliquoted and stored at −80° C.

Genital Tract Infections.

One week prior to infection, mice were treated with 2.5 mg of medroxyprogesterone delivered subcutaneously (Depo-Provera, Pfizer Pharmaceuticals, New York, N.Y.). Lightly anesthetized C57BL/6 female mice were infected vaginally with $5\times10^4$ inclusion forming units (IFU) of *C. muridarum* (Nigg) in 10 μl of SPG buffer. Mice were swabbed 7 days post infection and IFU quantified to document infection. Mice >6 weeks post infection were considered immune mice.

While in the foregoing embodiment the mice were artificially infected with the bacteria, a mammal with a naturally acquired infection could alternatively be used to derive the CD8 T cell clones. In such case, the CD8 T cell clones can be derived pursuant to the methods described herein after the infection has been given a sufficient time to allow for a T cell immune response in the infected mammal (typically longer than about two weeks).

*Chlamydia*-Specific CD8 T Cells.

After bacterial clearance, CD8 T cell clones were derived from immune splenocytes after expansion on irradiated immune splenocytes (the novel approach underpinning the inventions of the present disclosure) and *Chlamydia* antigen, with depletion of CD4 T cells, and cloning by limiting dilutions using either UV-inactivated *C. muridarum* (*mycoplasma*-free *Chlamydia muridarum* (Nigg) (MoPn)) or elementary body (EB)-depleted soluble *C. muridarum* antigen preparations as the stimulus (about 99.998% depletion of EB by centrifugation) as described in further detail below (see also the Johnson Publication).

T cell expansion cultures were performed in RPMI 1640 with 25 mM HEPES supplemented with 10% characterized fetal bovine serum (HyClone). 2 mM Lalanyl-L-glutamine (Glutamax I; Gibco/Invitrogen). 25 pg/mil gentamicin (Sigma), and $5\times10^{-5}$ M 2-mercaptoethanol (Sigma: St. Louis. Mo.): referred to as RPMI CM. Immune splenocytes harvested from mice were plated at $12.5\times10^6$ cells per well in tissue culture treated 12-well plates, in RPMI CM containing murine recombinant IL-1α (2 ηg/ml), IL-6 (2 ηg/ml), IL-7 (3 ηg/ml), IL-15 (4 ηg/ml), human recombinant IL-2 (100 units/ml) (Chiron Corp.: Emeryville Calif.), 20% 2° mixed lymphocyte culture supernatant, and 20 μl per well EB-depleted *C. muridarum* antigen (soluble antigen) or 20 ul of UV-inactivated *C. muridarum* (~7 million bacteria). Subsequent passages in 24-well plates used $2.5\times10^5$ T cells and $5\times10^5$-γ-irradiated (1200 rad) immune splenocytes APC and the same conditions as in the primary culture. CD4 T cells were depleted from polyclonal populations by magnetic bead separation per the manufacturer's protocol (Miltenyi Biotec; Auburn Calif.). The resulting polyclonal CD8 T cell populations were cloned by limiting dilution and passed weekly as above. Recombinant mouse cytokines were purchased from R&D Systems (Minneapolis, Minn.).

Activating lymphocytes from immune mice with immune-irradiated splenocytes pulsed with either UV-*C. muridarum* (uvMoPn) or the EB-depleted-infected-epithelial-cell lysates (soluble *Chlamydia* antigens (sAg)) yielded polyclonal T cell populations with small, but readily detectable. CD8 T cell populations (about 3% with uvMoPn: 10% with soluble antigen) (see FIG. 1, subpart A). CD4 T cells were selectively depleted from those polyclonal populations using magnetic bead technology and the remaining T cell populations were cloned by limiting dilution to derive two "UV-*C. muridarum*" CD8 T cell clones (labeled in subparts B and C of FIG. 1 and FIGS. 3A-4 as "8uvmo-1" and "8uvmo-2") and three "soluble antigen" CD8 T cell clones (labeled in subparts B and C of FIG. 1 and FIGS. 3A-4 as "sAg1" "sAg2" and "sAg3"; also referred to in this document as "8sAg1", "8sAg2", "8sAg3" respectively).

Flow Cytometry.

T cell clones were stained for 20 min on ice in RPMI CM with: Unconjugated 145-2c11 (CD3), FITC-coupled PE-coupled 53-5.8 (CD8β), PE-coupled 53-6.7 (CD8α) (BD Biosciences; San Jose Calif.), PE-coupled YTS191.1 (CD4) (Cedarlane Laboratories: Burlington. N.C.), FITC-coupled Mouse IgG2a (control antibody), PE-coupled Rat IgG2b (control antibody) (Ebioscience; San Diego. Calif.), FITC-coupled Goat anti-Armenian Hamster Ig (Jackson Immunoresearch Laboratories: West Grove Pa.). Cells were fixed with 1% paraformaldehyde after staining and subsequently analyzed on a FACSCalibur cytometer (BD Biosciences).

T cell Proliferation Assay.

$2.5 \times 10^5$ T cells were added to $2.5 \times 10^5$ γ-irradiated immune splenocytes (2000 rad) with antigen (UV-*C. muridarum* or sAg) and without (sucrose phosphate glutamate buffer; SPG) in 96 well u-bottom plates; wells pulsed with 0.5 μCi/well $^3$H-thymidine (ICN, Costa Mesa, Calif.) for 12 h at 36-48 h of the culture cycle. $^3$H-thymidine incorporation was measured with a TopCount beta counter (subpart B of FIG. 1).

T Cell Cytokine ELISAs.

For the specificity experiment in subpart C of FIG. 1, the conditions were the same as for the proliferation assay detailed above. For the MHC mapping experiments (FIGS. 2A-B), the conditions were the same except immune and naïve splenocytes were more lightly irradiated with 1000 rad (better antigen presentation capabilities) and all wells contained 1 ng/ml recombinant IL-7 to support T cell viability over the 72 h experiment. For cytokine polarization determination. T cells were activated by immobilized anti-CD3 antibody (145-2C11: NA/LE BD Pharmingen. San Jose. Calif.). Flat-bottom 96 well tissue culture plates were prepared by incubating 50 μl of 0.5 pg/ml 145-2C11 in PBS overnight at 4'C. Wells were washed once with media prior to use. $5 \times 10^4$ T cells were added to each well and supernatants collected at 24 h. Relative levels of IL-2, IL-5, IL-10, IL-13, IL-17, IFN-γ, and TNFα determined by ELISA using capture and biotinylated monoclonal antibody pairs with recombinant murine standards according to the manufacturer's protocols: IL-2 ELISA: 1A12 and 5H4, IFN-γ: XMG1.2 (Thermo Scientific; Rockford, Ill.): TNFα: TN3-19.12/ C1150-14; IL-10: JES5-2A5/SXC-1 (BD Biosciences: San Jose. Calif.); IL-13: Ebio13a/Ebio1316H, IL-5: TRFK4/ TRFK5 (Ebioscience; San Diego, Calif.). Recombinant murine IL-2, IL-10 (Thermo Scientific), IFN-γ (R&D Systems: Minneapolis, Minn.), IL-13 (Ebioscience) and IL-17a (Biolegend; San Diego, Calif.) were used as standards. Detection was accomplished with Streptavidin-HRP (BD Biosciences) and TMB substrate (Sigma); see FIG. 3A-B.

*Chlamydia* Replication Experiments.

C57epi.1 cell monolayers in 48-well plates were untreated or treated with IFN-γ (10 ηg/ml) for 14 h preinfection. Wells were infected with 3 inclusion forming units (IFU)/cell. After addition of *C. muridarum*, the plates were spun at 1200 rpm (300×g) for 30 min. Mock-infected wells received an equivalent volume of sucrose-phosphate-glutamate acid buffer lacking *C. muridarum*. Four hours post infection, the inocula were removed and $1.5 \times 10^5$ CD4 T cell clone cells were added per well. Twenty eight hours later. 32 h post infection, wells were scraped, harvested in sucrose phosphate buffer (SPG), and stored at −80° C. until titers could be determined on McCoy cell monolayers. (FIG. 4, subparts A-C)

As shown herein, conventional MHC class Ia—restricted *Chlamydia*-specific CD8 T cells do not appear to be the dominant CD8 T cell type in *Chlamydia*-specific T cell populations from immune mice. Indeed, the majority of the *Chlamydia*-specific CD8 T cell clones did not appear to be restricted by Ml IC class Ia molecules (see FIGS. 2A and 2B and, in particular, FIG. 2B). Specifically, three of the five C57BL/6-derived CD8 T cell clones were activated as well or better by MHC class Ia-deficient naïve splenocytes (KbDb) pulsed with uvMoPn as compared to those derived from syngeneic naïve C57BL/6 pulsed with uvMoPn. Furthermore, two atypical *Chlamydia*-specific CD8 T cells have an unusual cytokine polarization that includes combinations of IFN-γ, TNF-α, IL-10, and IL-13 (identified in FIG. 3A by arrows) representing the successful application of the methodology in the derivation of CD8IL-13 T cell clones.

Gene Expression Microarray Analysis

To understand the unique immunobiology of CD8IL-13 T cells, the two murine CD8IL-13 T cell clones (sAg1, sAg3) were compared to three conventional CD8 T cell clones (8uvmo-2, 8uvmo-3, and an alloreactive CD8 T cell clone CD8bm1) by gene expression micro array analysis in rested and activated states. Specifically, the T cell clones were purified by ficoll-hypaque (histopaque 1083; Sigma Chemical Co.) at the end of their culture cycle and then grown for 3 days in RPMI CM supplemented with 3 ng/ml recombinant mouse IL-7 without antigen stimulation (resting state) or activated for 14 h with immobilized anti-CD3 antibody (as in T cell cytokine methods) in RPMI CM (activated state). Total RNA was isolated from each T cell clone using a protocol that included an RNAse-free DNAse I treatment step (RNAeasy; Qiagen, Valencia. Calif.). With assistance from the Indiana University Center for Medical Genomics, gene expression patterns were analyzed using the Affymetrix Mouse ST 1.0 Array that analyzes 28,853 murine genes. Samples were labeled using the standard Affymetrix protocol for the WT Target Labeling and Control Reagents kit according to the Affymetrix user manual: GeneChip® Whole Transcript (WT) Sense Target Labeling Assay GeneChip. Individual labeled samples were hybridized to the Mouse Gene 1.0 ST GeneChips® for 17 hours then washed, stained and scanned with the standard protocol using Affymetrix GCOS (GeneChip® Operating System). GCOS was used to generate data (CEL files). Arrays were visually scanned for abnormalities or defects. CEL files were imported into Partek Genomics Suite (Partek, Inc. St. Louis.

Mo.). RMA signals were generated for the core probe sets using the RMA background correction, quantile normalization and summarization by Median Polish. Summarized signals for each probe set were log 2 transformed. These log 2 transformed signals were used for Principal Components Analysis, hierarchical clustering, and signal histograms to determine if there were any outlier arrays. Untransformed RMA signals were used for fold change calculations.

Data was analyzed using a 1-way Anova (analysis of variance) using log 2 transformed signals for all five CD8 T cell clones, and contrasts were made comparing CD8IL-13 T cell clones sAg1 and sAg3 to the conventional Chlamydia-specific CD8 T cell clones 8uvmo-2, 8uvmo-3, and the alloreactive CD8 T cell clone CD8bm1. Fold changes were calculated using the untransformed RMA signals. Genes up or down regulated >3-fold with p values <0.001 for CD8IL-13 T cells versus the conventional T cell clones are included in tables in FIGS. 6 and 8, and summarized in Table 1 below.

In relevant part, unique CD8IL-13 biomarkers in Table 1 were defined as being >3 fold different than the 3 conventional CD8 clones in both rested and activated states (1810011H11Rik (homolog of C10orf128). Arntl, Cep85L, Amelx, Epdr1). CD8IL-13 T cell clones in the activated state uniquely increased mRNA for IL-13 and IL-5, thus confirming that CD8IL-13 T cells produce both IL-13 and IL-5 when activated and therefore have a CD8IL13/5 phenotype. (see Table 1).

plate. Non-adherent cells were collected and "untouched" CD8 T cells isolated using a commercial magnetic bead kit (Miltenyi Biotech).

Total RNA was isolated from each subject's purified T cells using a protocol that included an RNase-free DNase I treatment step (RNAeasy; Qiagen, Valencia, Calif.). Specific mRNA gene reverse transcription and amplification were performed using AMV reverse transcriptase/Tfl DNA polymerase in a onestep system (AccessQuick RT-PCR; Promega, Madison, Wis.). Amplification conditions were 1) 48° C. for 45 min: 2) 95° C. for 2 min: 3) 95° C. for 30 s: 4) 57° C. for 20 s: 5) 72° C. for 30 s; 6) go to step 3 for X times; 7) 72° C. for 7 min: and 8) hold at 4° C. using an MJ Research J200 PCR machine. 250 ng of total RNA with 40 cycles was used for the CD8 (loading controls: expected PCR product 356 base pairs); 500 ng of total RNA with 42 cycles was used for the C10orf128. PCR reactions lacking reverse transcriptase (DNA contamination controls) for CD8 and C10orf128 reactions showed no PCR products (data not shown). Primer pairs used were CD8 (ccagtccaccttcctcctatac, gatatcacaggcgaagtccagc; PCR product 356 base pairs) and C10orf128 (atgaacttgggggtcagcatgct, agagtcgtcgtcaaataagtgcctc; PCR product 204 base pairs) sense and antisense primers using a one-step RT-PCR reagent (Access RT-PCR. Promega). Products of the RT-PCR reactions were separated on 2.5% agarose gels containing ethidium bromide (FIG. 9). Images of the gels were

TABLE 1

Mouse CD8IL-13 T cell genes.

| Mouse T cell clones Gene Symbol | CD8IL13+ vs CD8IL13− | | CD8IL13+ vs CD8IL13− & alloCD8 | | CD8IL13+ vs alloCD8 | | gene title |
|---|---|---|---|---|---|---|---|
| | p-value | Fold-Change | p-value | Fold-Change | p-value | Fold-Change | |
| CD8IL-13 unique genes identified in both "rested" and "activated" arrays | | | | | | | |
| 1810011H11Rik | 2.12E−15 | 24.85 | 1.52E−15 | 22.31 | 8.19E−14 | 20.03 | RIKEN cDNA 1810011H11 gene (C10orf128 homolog) |
| Arntl | 3.00E−08 | 12.80 | 5.51E−07 | 6.84 | 5.00E−04 | 3.65 | aryl hydrocarbon receptor nuclear translocator-like |
| Cep85l | 7.61E−04 | 4.88 | 7.67E−05 | 6.79 | 1.63E−04 | 9.44 | Cep85l centrosomal protein 85-like |
| Amelx | 1.57E−10 | 7.75 | 8.75E−12 | 10.68 | 4.13E−11 | 14.71 | amelogenin X chromosome |
| Epdr1 | 2.33E−04 | 5.60 | 1.36E−04 | 5.59 | 1.13E−03 | 5.59 | ependymin related protein 1 (zebrafish) |
| CDIL-13 unique cytokine genes identified only in the "activated" array | | | | | | | |
| Il5 | 1.32E−13 | 30.03 | 2.74E−14 | 31.69 | 1.30E−12 | 35.28 | interleukin 5 |
| Il13 | 3.00E−12 | 15.71 | 4.01E−13 | 17.95 | 7.98E−12 | 23.41 | interleukin 13 |

The five genes unique to murine CD8IL-13 T cell clones in both "resting" and "activated" arrays, and the two cytokines uniquely produced by murine CD8IL-13 T cells in the activated array. This gene expression micro array data defines the molecular fingerprint of CD8IL-13 T cells. Two CD8IL-13 T cell clones (sAg1 & sAg3) were compared to two conventional CD8 T cell clones (8uvmo-2 & 8uvmo-3) and one alloreactive CD8 T cell clone specific for H2-K$^{bm1}$ (CD8bm1) in the "rested" (9 days post passage) and "activated" (14 hours after activation with immobilized antibody specific for CD3) states. Five unique CD8IL-13 biomarkers, defined as those that differ between CD8IL-13 T cell clones and the other three conventional T cell clones by >3 fold in both the resting and activated states, were discovered including 1810011H11Rik (homolog of C10orf128), IL-13, IL-5, Arntl, Cep85L, Amelx, Epdr1. In the activated state, when T cells produce cytokines, there were two cytokines unique to CD8IL-13 T cells - IL-13 and IL-5.

RT-PCR.

The murine CD8IL-13 biomarker's relevance was also investigated with respect to human CD8 T cells. In a first investigation, peripheral blood CD8 T cell clones were purified from the peripheral blood of healthy human subjects (three), human subjects with systemic sclerosis (two), human subjects with acute Chlamydia infections (three), and one individual with a necrotizing granulomatous process of unclear etiology. The mononuclear fraction of blood was isolated utilizing Lymphoprep tubes. The mononuclear fraction from each subject was incubated RPMI 1640 CM for 40 minutes in 2 wells of a tissue culture-treated plastic 6 well inverted for presentation purposes. As shown in FIG. 9, the gels support the presence of C10orf128 mRNA in CD8 T cells circulating in the peripheral blood of the individuals with scleroderma.

Cell Sorting.

In a second investigation, two subjects were recruited—a healthy human male subject (control) and a subject with active scleroderma including severe sclerodactyly. 30 cc of blood was taken from each subject and the mononuclear fraction was isolated with Lymphoprep tubes. Purified mononuclear cells were adhered to tissue culture treated plates for 40 minutes at 37° C. in RPMI1640 CM. Non-adherent cells were recovered with pipetting and "untouched" CD8 T cells were then purified using magnetic bead separation (CD8+ T Cell Isolation Kit, human; Miltebiomarkers, CLC and ALOX5, were also identified as discussed below (see also Table 2).

TABLE 2

Human CD8IL-13 SSc Genes.

| | Micro array mRNA signal (arbitrary units) | | | | | | |
|---|---|---|---|---|---|---|---|
| Gene Symbol | SSc C10orf128 pos | Control C10orf128 pos | SSc C10rf128 neg | Control C10orf128 neg | SSc Ratio | SSc/Con ratio | Gene Title |
| C10orf128 | 131.64 | 49.36 | 61.41 | 45.81 | 1.99 | 19.78 | chromosome 10 open reading frame 128 |
| ARNTL | 157.58 | 132.76 | 74.48 | 120.59 | 1.92 | 6.83 | aryl hydrocarbon receptor nuclear translocator-like |
| CEP85L | 95.73 | 78.67 | 65.38 | 80.42 | 1.50 | −17.33 | centrosomal protein 85kDa-like |
| IL5 | 99.87 | 124.60 | 34.69 | 102.64 | 2.37 | 2.97 | interleukin 5 (colony-stimulating factor, eosinophil) |
| IL13 | 172.49 | 142.92 | 78.00 | 101.33 | 1.57 | 2.27 | interleukin 13 |
| CD226 | 892.03 | 605.84 | 603.47 | 752.36 | 1.84 | −1.97 | CD226 molecule |
| CLC | 123.61 | 62.05 | 22.60 | 43.36 | 3.82 | 5.40 | Charcot-Leyden crystal protein (galectin 10) |
| ALOX5 | 166.68 | 65.15 | 44.34 | 36.33 | 2.10 | 4.24 | arachidonate 5-lipoxygenase |

Gene expression micro array data demonstrating that C10orf128 positive CD8 T cells circulating in the peripheral blood of an SSc subject, but not a healthy control subject, are positive for 5 of 6 evaluable murine CD8IL-13 biomarkers shown in Table 1 (C10orf128, ARNTL, CEP85L, IL-5, IL-13; Amelx not represented in the human array), thereby validating C10orf128 as a unique cell surface biomarker for SSc CD8IL-13 T cells. CD226, a conventionally known CD8 SSc biomarker fell just below the identified cutoff for assignment (SSc ratio ≥1.5 and SSc/Con ratio >2), but is included as additional validation of the analysis methodology. The human micro array identifies two additional SSc CD8IL-13 genes that are diagnostic/therapeutic targets: CLC (galectin-10) a lysophospholipase measurable in serum that may serve as a convenient biomarker for CD8IL-13T cells. SSc disease activity and as a potential SSc disease modifying therapeutic target, and ALOX5, a hematospecific lipoxygenase with an existing specific inhibitor, VIA-2291, that has been investigated in Phase II clinical trials for coronary artery disease without demonstrable benefit.

nyi Biotech). The purified viable CD8 T cells were stained with the exemplary rabbit antiserum of the present disclosure that is, in at least one embodiment, specific for C10orf128, for CD8, and with a violet live/dead dye. CD8 T cells from the scleroderma subject (4 million) and the control subject (5 million) were sorted on a FACS Aria III isolating viable C10orf128 positive CD8 T cells (in toto) and C10orf128 negative T cells (1.5 million) as internal controls.

Total isolated C10orf128positive CD8 T cells were 120,000 scleroderma and 370.000 control (see FIGS. 11A and 11B). The gates for Facs Aria sorting were set intentionally to capture roughly 10% of the CD8 T cells that were the brightest for C10orf128 staining in gate P4: C10orf128negative CD8 T cells were captured in gate P5. Identical gates were used for sorting scleroderma and control CD8 T cells with final CD8-C10orf128positive cell gates capturing 7% and 15% of the total cells in gate P4 respectively. Total RNA was isolated from C10orf128positive and C10orf128 negative CD8 T cell pools and used for Affymetrix Human Gene 1.0 ST Array analysis.

The CD8pos C10orf128positive pool from the SSc subject contained the CD8IL-13 T cell subset based on enhanced mRNA levels for human homologs of murine CD8IL-13 unique biomarkers (summarized in Table 1) including C10orf128, Arntl, Cep85L, IL-13, and IL-5 as compared to the SSc C10orf128 negative pool, and the C10orf128positive and negative pools sorted from the healthy control subject. Two additional human CD8IL-13

Micro Array Data Analysis

Because successful RNA isolation, labeling, and hybridization requires sufficient RNA, the CD8-C10orf128 sort was performed to ensure enough recovered cells to meet the minimum RNA processing requirements. The majority of cells in the P4 gate (C10orf128 positive) were not CD8IL-13 T cells based on the presence of T cells the P4 gate of the healthy control where CD8IL-13 T cells are not expected. To address whether the C10orf128 sort was successful, i.e. the C10orf128 custom antibody worked, the data was analyzed pursuant to the following assumptions:

The level of C10orf128 mRNA (arbitrary fluorescence units) should be higher in the C10orf128 positive pool than the C10orf128 negative pool of the scleroderma subject; a C10orf128 positive/negative mRNA signal ratio was calculated utilizing the Healthy Control data as the "SSc ratio"=[SSc C10orf128pos/C10orf128 neg]/[Control C10orf128pos/C10orf128neg]) with a positive screening result arbitrarily defined as an SSc ratio of >=1.5.

TABLE 3

| Transcript ID | Gene Symbol | RO10H001 SSc C10orf128 pos | RO10H002 Con C10orf128 pos | RO10H003 SSc C10orf128 neg | RO10H004 Con C10orf128 neg | SSc Ratio C10orf128pos/neg | SSc/Con ratio |
| --- | --- | --- | --- | --- | --- | --- | --- |
| 16714104 | C10orf128 | 131.637 | 49.3585 | 61.4069 | 45.8087 | 1.989513163 | 19.78424137 |

As shown above in Table 3, the SSc ratio for C10orf128 mRNA signal was 1.989 in the scleroderma subject: the sort based on CD8 and C10orf128 was considered successful. In the healthy control subject, the C10orf128 mRNA signal was not enhanced by sorting for C10orf128pos cells, i.e. the C10orf128 mRNA signal was low and similar in the Healthy Control C10orf128 positive (49.3 arbitrary units) and C10orf128 negative pools (45.8 units). There were not sufficient "true" C10orf128 positive T cells in the control subject to generate a C10orf128 mRNA signal, and this result thereby defined "background noise" as it relates to CD8IL-13 T cells in this assay.

This information was then used to define a second criterion for CD8IL-13-specific transcripts based on premise that (Con C10orf128pos pool signal)–(Con C10orf128neg pool signal) in the Healthy Control subject would a small number based on lack of a significant CD8IL-13 T cell signal: that small number was empirically close to I based on the raw data. Conversely, in the scleroderma subject for CD8IL-13-specific gene transcripts, e.g., C10orf128, the subtraction (SSc C10orf128pos signal–SSc C10orf128neg signal) would yield a number significantly greater than 1. A second screening criterion was defined and called the SSc/Con ratio: (SSc C10orf128pos –SSc C10orf128neg)/(Con C10orf128pos–Con C10orf128neg). An arbitrary SSc/Con ratio value of 2 (positive or negative) was used to identify putative CD8IL-13 gene transcripts. The SSc/Con ratio cutoff of 2 eliminated 97% of the transcripts in the Human ST 1.0 micro array from further consideration.

Applying the "SSc ratio" and "SSc/Con ratio" criteria to the raw data yielded 26 putative CD8IL-13 genes whose mRNA levels were enhanced in the CD8posC10orf128pos pool of the Scleroderma subject compared to the other three sorted CD8 T cells pools in the sort-micro array (SSc CD8posC10orf128neg, Healthy Control CD8posC10orf128pos & CD8posC10orf128neg). Five of the 26 genes were definitively CD8IL-13 T cell biomarkers based on the inventor's mouse CD8IL-13 data (C10orf128, ARNTL, CEP85L, IL-5, IL-13; see Table 1). 4 additional genes, CD38, Ki-67. Interferon-gamma (IFN-g is produced by mouse CD8IL-13 T cells. FIG. 3A), reflect a higher activation state in the disease-causing CD8 T cells from the Scleroderma subject compared to normal CD8 T cells from a healthy control, an expected result for an active inflammatory disease. Additionally, for validation purposes, the recently identified CD8 scleroderma biomarker CD226 had a SSc ratio of 1.84 (meets inclusion criterion #1) and an SSc/Con ratio of –1.97 (did not meet criterion #2) and was excluded by the analysis we employed.

CD226 demonstrates that the analysis stringency applied to our data set was set appropriately to identify genes that were unique to CD8IL-13 T cells in gate P4 of the Scleroderma subject FIG. 11A. Closer scrutiny of CD226 in Table 2 shows that it had an enhanced mRNA signal in the SSc subject, but CD226 has a high fluorescence signal in all the CD8 T cell pools making it a less than ideal CD8IL-3 biomarker based on mRNA levels.

Addressing whether the conclusions above are appropriate based on statistical considerations: If screening criteria #1 and #2 have nothing to do with CD8IL-13 T cell biology the likelihood of an individual gene being randomly selected in our screen is 26 "random genes"/36.079 transcripts analyzed in the micro array, or 0.07%. Selecting out 5 of 6 definitive mouse CD8IL-13 biomarkers, and nine genes in total that almost certainly reflect CD8IL-13 T cell biology, is roughly a 1-in-a-million event utilizing a Bonferoni correction for 36,079 tests. Accordingly, the human C10orf128 sort micro array data validates that the custom antibody to C10orf128 disclosed herein, in combination with antibody to CD8, uniquely identified human CD8IL-13 T cells within the peripheral blood of the Scleroderma subject. Based on this data, such custom antibody could also be used to stain biopsy tissues and identify human CD8IL-13 T cells therein.

As described herein, the present disclosure establishes that CD8IL-13 T cells at the population level produce IL-13 and IL-5 when activated. CD8 T cells that produce IL-13 are rare; in humans they have only been described in scleroderma where it is unknown whether they also produce IL-5, and more recently in tuberculosis. In tuberculosis patients, Mycobacterium tuberculosis-specific CD8IL-13 T cells were not restricted by conventional HLA class Ia and were polarized to produce IL-13 and IL-5: data that parallels the inventor's mouse Chlamydia and human SSc micro array data. Indeed, while the C10orf128 sort can purify/remove CD8IL13/5 T cells from the peripheral blood of a patient with SSc, it does not identify/purify/remove CD8IL13/5 T cells from the peripheral blood of the healthy control subject; thus demonstrating that CD8IL13/5 T cells are a minority T cell subset uniquely expanded in patients experiencing an active condition mediated by CD8IL-13 T cells such as, for example, SSc patients. In such cases, the CD8IL-13 T cells that can be targeted using anti-C10orf128 therapy for the purpose of ameliorating the disease manifestations using an approach analogous to alemtuzumab (CamPath) directed against CD52 (61 amino acid cell surface protein) to deplete circulating tumor cells in B-cell chronic lymphocytic leukemia.

Made possible by the novel findings outlined herein, exemplary compositions and methods are provided for the diagnosis and/or treatment of one or more disease states mediated by a subset of CD8 T cells that produce IL-13 when activated. Such disease states may include, for example and without limitation, inflammatory disease states such as systemic sclerosis.

Because subjects experiencing an active condition mediated by CD8IL-13 T cells can have significant expansion of CD8IL-13 T cells and expression (i.e. elevated or upregulated) of at least the CD8IL-13 biomarker C10orf128 in their peripheral blood as compared to a healthy individual, identifying this upregulation would be exceedingly useful as a minimally invasive—yet effective and accurate—diagnostic indicator. However, for such a method to be successful (clinically or otherwise), one must effectively identify, or isolate and purify, the CD8IL-13 T cells in or from the peripheral blood respectively.

In at least one exemplary embodiment of the present disclosure, a novel antisera to the putative extracellular domain of C10orf128 is provided to achieve this end. Furthermore, methods are also provided for the production of such a C10orf28-specific antisera formulated to isolate C10orf128 positive CD8 T cells from a peripheral blood or other sample (e.g., a biopsy sample). In application, the novel antisera described herein may be used to identify a subset of CD8 T cells that make IL-13 upon activation and/or to purify from peripheral blood a subset of CD8 T cells that make IL-13 upon activation.

Method 1200 comprises a method for the production of C10orf128-specific antisera. It will be appreciated that the antisera hereof may be produced pursuant to antisera production methodologies known in the art or hereinafter developed, provided that the antisera is made against a peptide having an amino acid sequence comprising QVLATGKTPGAEIDFKY (SEQ ID No. 1) or a functional equivalent, variant or fragment thereof. SEQ ID No. 1 is the human homolog of the mouse CD8IL-13 cell surface biomarker 1810011H11Rik's predicted extracellular domain.

For example, step 1202 of method 1200 may comprise injecting a sample that includes a peptide having an amino acid sequence comprising SEQ ID No. 1 into an animal. In addition to SEQ ID No. 1, the sample may also comprise an adjuvant mixture as is known in the art. Additionally or alternatively, a cysteine may be added to SEQ ID No. 1 to couple SEQ ID No. 1 to a keyhole limpet hemocyanin (KHL) (e.g., CQVLATGKTPGAEIDFKY). In at least one exemplary embodiment, using a commercial vendor, rabbits may be injected with SEQ ID No. 1 coupled to a KLH in adjuvant according to the vendor's protocol at step 1202.

After the initial injection into the animal at step 1202, the animal undergoes a primary immune response that procures a relatively low titer antiserum at step 1204. After a period of time, injection step 1202 is repeated (i.e. booster) at step 1206 such that the animal undergoes a secondary immune response. Step 1206 (the booster step) may be repeated as many times as necessary or appropriate to achieve the desired titer of the antisera. At step 1208, the antiserum is withdrawn from the animal.

Method 1200 may optionally include step 1210, which comprises purifying the antiserum pursuant to known processes prior to use. For example, in at least one embodiment, step 1210 comprises purifying antibodies specific for SEQ ID No. 1 on an affinity column based on SEQ ID No. 1.

Accordingly, the resulting antisera comprises a C10orf128 antibody specific for the cell surface domain of biomarker C10orf128 and, thus, is capable of recognizing SEQ. ID No. 1, or a functional equivalent, variant or fragment thereof and isolating the same. It will be appreciated that alternative coupling strategies could also be employed (including, but not limited to, C-terminal coupling) such that the peptide having an amino acid sequence comprising SEQ ID No. 1 can be covalently attached to a carrier protein and used for immunization purposes. As previously noted, method 1200 need not comprise the exact steps described above, but instead the antisera may be prepared in any customary manner with the aid of experimental animals. In at least one embodiment, the antisera may comprise rabbit antisera. Alternatively, the animal may comprise a rat, hamster, chicken, goat, or any other appropriate animal.

Furthermore, in at least one exemplary embodiment, the resulting antiserum composition may be further processed at optional step 1212. In at least one embodiment, step 1212 comprises passing the purified SEQ ID No. 1 antibodies over an affinity column based on the scrambled peptide sequence comprising SEQ ID No. 2 (or a functional equivalent or variant thereof (i.e. other scrambled peptides) to remove unwanted antibodies that non-specifically bind SEQ ID No. 1 by cross absorption. This step 1212 improves specificity, and antibodies that flowed through the SEQ ID No. 2 (or functional variant thereof) column may be used as specific reagents for binding human C10orf128.

In another embodiment, the intact QVLATGKTPGAEIDFKY (SEQ ID No. 1) or a functional equivalent peptide may be used to generate a monoclonal antibody specific for C10orf128 utilizing mice, rats, hamsters, rabbits or other mammalian species, and/or recombinant DNA techniques may be used to humanize any C10orf128-specific antibody as technologies evolve.

In at least one alternative embodiment, the antiserum may comprise a monoclonal antibody derived from a mammalian animal host or a C10orf128-specific immunoglobulin comprising messenger ribonucleic acid or protein sequences determined by molecular techniques. There, such molecular techniques may comprise powerful RNA sequence type technologies capable of obtaining mRNA sequences of antibodies by purifying antigen-specific B cells and subsequently performing single cell sequencing. Through leveraging these powerful molecular techniques in connection with an alternative embodiment, the method may alternatively comprise immunizing a mammal (e.g., a mouse) with the peptide having an amino acid sequence comprising SEQ ID No. 1 (or a functional equivalent or variation thereof), purifying B cells collected from such mammal that bind to the aforementioned peptide, performing single RNA sequencing on a number of such B cells (e.g., 100), and using the resulting genomic data to synthesize the critical heavy and light chain residues, thereby resulting in a C10orf128-specific antibody. Notably, the resulting antibody can be prepared without performing a hydridoma-fusion step and such antibody may already be humanized.

Among other things, this C10orf128-specific antisera allow s for the development of novel diagnostics and interventions for active conditions mediated by CD8IL-13 T cells. For example, C10orf128 positive and negative CD8 T cells identified by flow cytometry (CD8lowC10orf128pos) or purified through use of the antisera of the present disclosure can now be quantified, and/or subjected to RT-PCR or gene expression microarray analysis to identify and diagnose active disease conditions, as well as possible targets for therapeutic interventions.

FIG. 13 shows a flow chart of at least one exemplary embodiment of a method 1300 for diagnosing an active condition mediated by CD8IL-13 or CD8IL13/5 T cells. Notably, method 1300 may be noninvasive. As previously described herein, the expression of certain newly identified biomarkers is elevated when a human subject experiences an active condition mediated by CD8IL-13 or CD8IL3/5 T cells. These biomarkers may include, for example, C10orf128, IL-13, IL-5, Arntl, Cep85L, Amelx, Clc, and/or Alox5.

Method 1300 comprises a purification step 1302. At step 1302, a population of CD8 T cells collected from a sample of blood are purified. The blood sample may be mammalian blood and, in at least one exemplary embodiment, the blood sample comprises peripheral blood collected from a human subject (either from a blood draw or otherwise). Likewise, the population of CD8 T cells may comprise a circulating CD8 T cell population from the peripheral blood mononuclear cell fraction taken a from subject.

Purifying the population of CD8 T cells at step 1302 may be achieved through any method now known in the art or hereinafter developed that can achieve this purpose. In at least one embodiment, step 1302 comprises utilizing magnetic bead purification methods. In another embodiment, step 1302 involves flow cytometry sorting. Additionally or alternatively, the CD8IL-13 T cell population may be directly purified using the C10orf128-specific antisera described herein.

It will also be recognized by one of skill in the art that homologs of the biomarkers described herein may also be similarly used to identify and/or purify a subset of CD8 T cells that make IL-13 upon activation (e.g., mouse 18101H11Rik and its human analog C10orf128). For example, in at least one exemplary application, one of skill in the art could use the methodologies and techniques described herein to purify CD8 T cells from scleroderma patients or other human subjects, activate such cells (using one or more of the methodologies described herein including, but not limited to, immobilized anti-CD3. PMA/ionophores), and sort the cells based on the human homologs of the mouse "activated" CD8IL-13 cell surface biomarkers Tm4sf19 or I830127L07Rik.

At step 1304, mRNA is isolated from the purified CD8 T cells and, at step 1306, the expression of one or more targeted biomarkers is quantified in the isolated mRNA. RNA isolation and biomarker quantification may both be performed in accordance with conventional techniques known in the art. In at least one embodiment, for example, the step of 1304 may be performed using phenol-chloroform extraction, using commercially available kits, and/or through any other known technique. In another embodiment purified CD8 T cells or directly purified C10orf128 pos T cells are used directly or proteins extracted for quantitation. Additionally or alternatively, T cells purified utilizing a biomarker may be activated.

Likewise, quantifying the expression of one or more targeted biomarkers at step 1306 may also be performed using conventional methods. In at least one embodiment, step 1306 comprises using flow cytometry and/or producing a semi-quantitative visualization of the level of expression of the targeted biomarker(s) on ethidium bromide-containing agarose gels (e.g., via semiquantitative gel electrophoresis). Optionally, step 1306 may also comprise performing quantitative reverse transcriptase polymerase chain reaction (RT-PCR) on the isolated RNA. In another embodiment, the biomarker proteins are quantified using ELISA, mass spectroscopy, immunofluorescence, or using another protein-based methodology. In another embodiment IL13 and/or IL-15 released by biomarker-purified T cells is/are quantified using enzyme-linked immunosorbent assay (ELISA), enzyme-linked immunospot (Elispot), Luminex, or similar technologies. As described in detail herein, such biomarkers may comprise one or more of the following: C10orf128, IL-13, IL-5, Arntl, Cep85L, Amelx, Clc, and/or Alox5 and/or any other biomarker that is up or downregulated in response to activated CD8IL-13 T cells.

Step 1308 comprises comparing the quantified level of expression of the targeted biomarker(s) with a baseline level of expression established for each of the one or more biomarkers in question. Biomarker levels can be established for normal/health subjects and can then be used to diagnose disease conditions. In at least one embodiment, any expression of the targeted biomarker(s) that is greater than an identified baseline is indicative of the subject experiencing an active condition or disease state mediated by a subset of CD8 T cells that are polarized to produce IL-13 (and, in at least one exemplary embodiment, IL-5 as well). As such, if the quantified level(s) of expression of the targeted biomarker(s) satisfy or exceed the established standard, step 1308 may result in a diagnosis of a medical condition.

In at least one exemplary embodiment, the baseline may be established as the relevant biomarker expression level in a healthy individual. Additionally or alternatively, a scale may be established with respect to one or more biomarkers under investigation. For example, a subject biomarker must be greater than or equal to 1.5 times the level of expression in a healthy individual to be indicative of the subject experiencing an active disease state. It will be appreciated that these baselines and scaling may be determined pursuant to available data, specific methodologies and parameters chosen for comparison, or at the direction of an investigator or medical provider.

In the event it is determined at step 1308 that the subject from which the sample was taken is experiencing an active disease state mediated by a subset of CD8 T cells (e.g., CD8IL-13 or CD8IL13/5) (i.e. a medical condition is diagnosed or supported), method 1300 may further comprise step 1310. At step 1310, therapeutic treatment is administered to the subject.

In at least one exemplary embodiment where the subset of CD8 T cells comprises CD8IL13 and/or CD8IL13/5 T cells, the therapeutic treatment may comprise an immunotherapy treatment that targets the subset of such T cells (e.g., using anti-C10orf128 biologics). Analogous to the administration of alemtuzumab (CamPath), which is directed against CD52 (a 61 amino acid cell surface protein) to deplete circulating tumor cells in B-cell chronic lymphocytic leukemia, such immunotherapy treatment may comprise administering an anti-C10orf128 monoclonal antibody for the purpose of ameliorating the disease manifestations of the active disease state. Following administration at step 1310, the anti-C10orf128 monoclonal antibody binds to the C10orf128 cell surface protein and depletes circulating CD8IL-13 and/or CD8IL13/5 T cells (i.e. the subset of cells mediating the active disease state).

In another embodiment and as supported by the human micro array data set forth in Table 2 hereof, the therapeutic intervention of step 1310 may comprise administering a compound formulated to inhibit therapeutic target Alox5. In such cases, for example, this step 1310 may be achieved by administering a therapeutically effective amount/dose of inhibitor VIA-2291 or another Alox5 inhibitor.

Examples of disease manifestations and/or active disease states with which this therapeutic step 1310 may be effective include any disease state mediated by CD8IL13 and/or CD8IL13/5 T cells including, without limitation, an active inflammatory disease state such as *Chlamydia*, scleroderma, and other rheumatologic illnesses. Furthermore, while step 1310 is described herein in connection with method 1300, it will be appreciated that therapeutic treatment step 1310 may itself comprise a method for treatment comprising the step of administering a therapeutically effective amount/dose of an inhibitor formulated to inhibit and/or deplete circulating CD8IL-13 and/or CD8IL13/5 T cells.

In at least one exemplary embodiment, an iteration of method 1300 may be performed to diagnose (and optionally treat) a rheumatologic illness in a mammal. FIG. 14 shows at least one example of such a method 1400. There, a sample is obtained from a mammal at step 1402. In at least one embodiment, the sample may comprise a blood sample and the mammal may comprise a human. Additionally, in at least one exemplary embodiment, the sample may comprise blood serum. Step 1402 may also comprise purifying a population of CD8 T cells from the sample if desired and/or appropriate in connection with the particular application of the method 1400.

At step 1404, the sample (or population of purified CD8 T cells thereof) is analyzed using techniques now known in the art or hereinafter developed to quantify the level of expression of Clc—otherwise known as galectin 10. For example, similar to steps 1304 and 1306 of method 1300, mRNA may be isolated from the purified CD8 T cells using commercially available kits and Clc biomarker expression may be subsequently quantified using RT-PCR. Real-time RT-PCR, or array technologies. Alternatively, step 1404 may comprise analyzing directly purified C10orf128pos T cells or proteins extracted therefrom for the quantitation of Clc expression using ELISA, mass spectroscopy, immunofluorescence, or another protein-based methodology. Alternatively step 1404 may comprise directly measuring the level of Clc in serum by ELISA or other protein-based technology.

At step 1406 (similar to step 1308 of method 1300), the level of expression of Clc is compared against an established control (e.g., a level of expression of Clc in a healthy, control subject or any other established guideline or scale). If an elevated level of Clc is detected within the sample, at step 1408, the subject mammal is diagnosed with a medical condition. In at least one exemplary embodiment, the medical condition may comprise a rheumatologic illness such as, for example and without limitation, scleroderma. If step 1408 of method 1400 indicates a positive diagnosis for a medical condition, the method 1400 may further comprise optional treatment step 1410. In at least one embodiment, treatment step 1410 may comprise administering a therapeutic treatment for the medical condition.

Now referring to FIG. 15, a flow chart representative of a method 1500 for analyzing small molecule efficacy in disrupting CD8IL-13 pathophysiology is shown. In at least one exemplary embodiment, method 1500 may be used to test and/or screen for the efficacy of inhibitors or other compounds to assess such inhibitors '/compounds' influence on the survival, proliferation, and/or cytokine production of a subset of CD8IL13 T cells in vitro and/or in vivo.

At step 1502, method 1500 comprises administering a formulated compound to a test subject experiencing one or more disease manifestations mediated by CD8IL-13 T cells. In at least one exemplary embodiment, such formulated compound comprises an active ingredient comprising a biomarker inhibitor (e.g., Alox5 inhibitors or any other inhibitors to the biomarkers described herein) and/or a compound (novel or otherwise) under investigation as a potential therapeutic agent.

Following administration, the test subject (or a sample therefrom) is analyzed at step 1504 to determine if the formulated compound had a measurable effect/parameter on CD8IL-13 T cells associated with the one or more disease manifestations mediated by the CD8IL-13 T cells. Examples of a measurable effect and/or parameter include, without limitation, an influence on the frequency, survival, proliferation, cytokine production of the CD8IL-13 T cells of a subject, and/or any other measurable markers as may be desired or appropriate. If a measurable effect is detected, the measurable effect may also be quantified at step 1504 and compared to an established standard. If, at step 1504, no measurable effect is detected or a measurable effect is detected but does not satisfy an established standard, the method may advance to step 1505 where the formulated compound is identified as ineffective at disrupting CD8IL-13 pathophysiology. Accordingly, in at least one embodiment, at step 1505 a determination is made that the compound is unlikely to be a therapeutic agent for such disease mediated by CD8IL-13 T cells.

Alternatively, the method 1500 may optionally advance to step 1506. At step 1506, the formulation of the formulated compound is modified into a subsequent iteration in an effort to achieve the desired measurable effect and/or quantification thereof. For example, the titration of the active ingredient(s) of the formulated compound (e.g., biomarker inhibitor and/or compound being tested) may be modified and/or other changes may be made as are known in the relevant arts.

Steps 1502-1506 may be repeated as many times as necessary or desired to either satisfy the established standard and/or confirm the active ingredient(s) is/are not effective to ameliorate the disease manifestations mediated by CD8IL13 T cell and/or to disrupt CD8IL13 pathophysiology. If/when a measurable effect is detected at step 1504 that satisfies the established standard, the method 1500 advances to step 1508 and the respective iteration of the formulated compound and/or active ingredient thereof is identified as effective in disrupting CD8IL-13 pathophysiology. Accordingly, at step 1508, a determination is made to advance the compound for further testing or therapeutic trials for approval.

Specific examples using the methods and materials described above will now be discussed in further detail.

Example 1

Derivation of *Chlamydia*-Specific CD8 T Cells Required Immune Splenocyte APC

To better understand *Chlamydia* pathogenesis. *Chlamydia*-specific T cell clones were derived from immune mice using UV-inactivated-*C. muridarum*-pulsed irradiated naïve splenocytes as antigen presenting cells (APC). Under those conditions, polyclonal T cell cultures were about 100% CD4 T cells (see FIG. 5). Isolating *Chlamydia*-specific CD8 T cells clones from mice was performed in order to study their immunobiology and compare them with *Chlamydia*-specific CD8 T cells that have been described in humans. An alternative culture system based on immune Ig-receptor-bearing APC may utilize cross-presentation pathways to generate more CD8 T cell epitopes and promote greater expansion of CD8 T cells. Activating lymphocytes from immune mice with irradiated immune splenocytes pulsed with either UV-*C. muridarum* (uvMoPn) or the EB-depleted-infected-epithelial-cell lysates (soluble *Chlamydia* antigens (sAg)) yielded polyclonal T cell populations with small, but readily detectable, CD8 T cell populations (see FIG. 1, subpart A): this is methodology for ex vivo expansion and isolation of T cells that has not previously been described in published literature that made possible isolation of CD8IL-13 T cells.

Irradiated immune splenocytes pulsed with UV-inactivated-*C. muridarum* expanded a small, but detectable, CD8 T cell population (~3%), while those irradiated immune splenocytes pulsed with sAg expanded a bit larger detectable CD8 T cell population (~10%) (subpart A of FIG. 1). CD4 T cells were selectively depleted from both of those polyclonal populations using magnetic bead technology, and the remaining T cell populations cloned by limiting dilution to derive two "UV-*C. muridarum*" CD8 T cell clones (labeled in the Figure as "8uvmo-1" and "8uvmo-2") and three "soluble antigen" CD8 T cell clones (which are labeled in the Figure as "8sAg-1," "8sAg-2" and "8sAg-3"). Accordingly, CD8 clones from 2 mice were isolated by limiting dilution after CD4 T cell depletion from polyclonal populations by magnetic bead separation. The resulting five *Chlamydia*-specific CD8 clones specifically recognized infected C57BL/6 oviduct epithelial cells over uninfected controls (subpart C of FIG. 4) and recognized *Chlamydia* antigen-pulsed immune syngeneic splenocytes (subparts B and C of FIG. 1).

As shown herein (see Example 5 below), conventional MHC class Ia—restricted *Chlamydia*-specific CD8 T cells are not the dominant CD8 T cell type in *Chlamydia*-specific T cell populations expanded from immune mice. Indeed, the majority of the *Chlamydia*-specific CD8 T cell clones are not restricted by MHC class Ia molecules (see FIG. 2B); the same was true in two independent investigations of human *Chlamydia*-specific CD8 T cell clones isolated from infected individuals. Specifically, three of the five mouse CD8 T cell clones (8sAg-1, -2, -3) were activated as well or better by Balb/c and MHC class Ia deficient naïve splenocytes pulsed with uvMoPn as compared to those derived from syngeniec naïve C57BL/6 pulsed with uvMoPn. Furthermore, two atypical *Chlamydia*-specific CD8 T cells exhibited an unusual cytokine polarization that included combinations of IFN-γ, TNF-α, IL-10, and IL-13 (FIG. 3A), representing the successful application of the methodology described herein.

Here, the CD8 T cell clones had varying abilities to terminate *Chlamydia* replication in epithelial cells (see FIG. 4, subparts A-B). 8uvmo-2 and 8uvmo-3 were effective in terminating *C. muridarum* replication: however, 8sAg-1, 8sAg-2, and 8sAg-3 were unable or inefficient at terminating replication even when the epithelial monolayers were pretreated with IFN-γ. Finally and summarily, as illustrated in FIG. 3A, two of the five CD8 T cell clones produced large amounts of IL-13 in addition to IL-2, TNF-α, IL-10, and IFN-γ.

As previously noted. IL-13 producing *Chlamydia*-specific CD8 T cells may contribute to immunopathology during *C. muridarum* genital tract infections based on the roles of TNF-α and IL-13 in scar formation. Specifically, data shows that TNF-α is associated with immunopathology and IL-13 is detrimental to *Chlamydia* clearance and associated with fibrosis and residual scarring. CD8 T cells producing IL-10, IL-13 and TNF-α are interesting with respect to immunopathology because in addition to a role for IL-10 in scarring, the combination of TNF-α and IL-13 is the underlying mechanism for bleomycin-induced pulmonary fibrosis and TNBS-induced colonic fibrosis in mouse models. Further. IL-13 expressing CD8 T cells have been found to mediate immunopathology in systemic sclerosis, a rheumatologic disorder that manifests as progressive scarring of the skin, and *Chlamydia*-specific CD8 T cells making IL-10, IL-13 and TNF-α may contribute to the CD8-mediated immunopathology observed in experimental murine genital tract infections. Accordingly, the atypical CD8 T cell clones described herein may be an important effector T cell subset for *Chlamydia*-associated immunopathology and representative of the atypical CD8 T cells in humans.

Example 2

*Chlamydia*-Specific CD8 IL-13 T Cell Clones Compared with Conventional CD8 T Cell Clones

*Chlamydia*-specific CD8 IL-13 T cell clones were compared with conventional CD8 T cell clones. CD8 T cell clones were grown under their usual culture conditions. At the end of the culture cycle the T cells were harvested and purified by ficoll-hypaque centrifugation to remove debris. The purified T cell clones were grown under non-activating conditions with recombinant murine IL-7 for 72 hours, then total RNA harvested and analyzed with Affymetrix Mouse ST 1.0 Array as described in Johnson R M, Kerr M S, Slaven J E. *Plac8-dependent and inducible NO synthase-dependent mechanisms clear Chlamydia muridarum infections from the genital tract*. J. Immunol. 2012 Feb. 15; 188(4): 1896-904. To investigate CD8IL-13 gene expression after T cell activation, the same microarray experiment previously described was repeated harvesting total RNA 14 h after activation by immobilized anti-CD3 monoclonal antibody. Gene expression microarrays were used to identify biomarkers and potential therapeutic targets in both resting and activated CD8IL-13 T cells.

Referring to FIGS. 6-8, Affymetrix gene expression microarray comparison is shown of two *Chlamydia*-specific CD8IL-13 T cell clones versus two *Chlamydia*-specific CD8 T cell clones that do not produce IL-13 plus a conventional alloreactive CD8 T cell clone specific for H-2K$^{bm1}$ that does not produce IL-13 (column labeled: Fold-Change (CD8IL3+ vs. CD8IL13- and allo CD8)): comparison of two *Chlamydia*-specific CD8IL-13 T cell clones versus two *Chlamydia*-specific CD8 T cell clones that do not produce IL-13 (column labeled: Fold-Change (CD8IL13+ vs. CD8IL13-)); comparison of two *Chlamydia*-specific CD8IL-13 T cell clones versus a conventional alloreactive CD8 T cell clone specific for H-2K$^{bm1}$ (column labeled: Fold-Change (CD8IL13+ vs. allo CD8)).

Example 3

CD8IL-13 is a Subset of CD8 T Cells with Enhanced Expression of 1810011H11Rik, Amelx, Dclk3, Mtmr7, Arntl, Sulf2, Pr2c5, CCR8 and Hpgds As supported by the results shown in FIGS. 6 and 7, resting CD8IL-13 T cells had unique expression of 1810011H11Rik, Amelx, Dclk3, Mtmr7, Ccr8, Arntl, Sulf2, Prl2c5, Hpgds. As supported by FIG. 8, activation of CD8IL-13 T cells identified unique and expected IL-13 production, unexpected IL-5 production, unique cell surface biomarkers Tm4sf19 & I830127L07Rik, and the anti-bacterial protein cathepsin G in addition to previously identified resting CD8IL-13 biomarkers 1810011H11Rik, Amelx, Arntl, Gm9766 (Cep851), Epdr1. The activated CD8IL-13 T cells had uniquely elevated mRNA for Mest, Mcc and Hcn1 whose biological significance in the T cell phenotype is unknown.

To investigate the mechanism underlying CD8 immunopathology. *Chlamydia*-specific CD8 T cell clones were isolated from mice that self-cleared genital tract infections. *Chlamydia*-specific CD8 T cell clones could not be derived with antigen-pulsed irradiated naïve splenocytes; instead derivation required use of irradiated immune splenocyte antigen presenting cells (APC). The majority of *Chlamydia*-specific CD8 T cell clones were not restricted by MHC class Ia molecules and had varying abilities to terminate *Chlamydia* replication in epithelial cells. Two of the five CD8 clones produced IL-13 in addition to IL-2, TNFα, IL-10, and IFN-γ, IL-13 producing *Chlamydia*-specific CD8 T cells may contribute to immunopathology during *C. muridarum* genital tract infections based on the roles of TNFα and IL-13 in scar formation.

Two *Chlamydia*-specific CD8 T cell clones were derived from immune mice infected previously with *C. muridarum* lacked MHC class Ia restriction and had cytokine polarization patterns that included TNF-α and IL-13, and had a novel gene expression pattern.

Example 4

Three *Chlamydia*-Specific CD8 T Cell Clones are not Restricted by MHC Class Ia Molecules In two previous independent human studies the majority of *Chlamydia*-specific CD8 T cells isolated from individuals with *C. trachomatis* genital tract infections were not restricted by HLA class Ia molecules. In that context, determining the restriction element for the five murine CD8 T cell clones was investigated.

Irradiated immune splenocytes produce cytokines capable of supporting antigen-independent proliferation and IFN-γ production, making them ill-suited for MHC restriction mapping. However, irradiated naïve splenocytes pulsed with *Chlamydia* antigens do not produce measurable cytokines and did not support meaningful antigen-independent IFN-γ production by bystander T cells.

Whether the CD8 T cell clones were MHC class Ia restricted was tested by comparing activation of mock-pulsed and UV-inactivated *C. muridarum*-pulsed irradiated nave splenocytes from C57BL/6 (wild type H-$2^b$) and K$^b$D$^b$ dual knockout mice (H-$2^b$; no MHC class Ia molecules) (FIG. 2B). K$^b$D$^b$ knockout splenocytes lacking MHC class Ia molecules were as competent as wild type splenocytes for activating three of the CD8 T cell clones, 8sAg1, 8sAg2, 8sAg3: while 8uvmo-2 and 8uvmo-3 were not significantly activated by antigen-pulsed naïve splenocytes. The majority of CD8 T cell clones (3 of 5) were not restricted by MHC class Ia: consistent with published human *Chlamydia*-specific CD8 T cell clone data.

Example 5

The CD8 Clones have Varying Abilities to Terminate *Chlamydia* Replication in Epithelial Cells

*Chlamydia*-specific CD4 T cell clones have varying abilities to terminate *Chlamydia* replication in epithelial cells. The ability of the CD8 T cell clones to terminate *Chlamydia* replication was tested in epithelial cells. C57epi.1 cells, untreated or pretreated with IFN-γ, were infected with *C. muridarum* at 3 IFU per cell. Four hours later the inocula were removed, monolayers washed, and T cell clones added to each well at an effector to target ratio of ~0.75:1. Wells were harvested at 32 h post infection and recovered IFU quantified on McCoy monolayers (FIG. 4, subparts A and B). 8uvmo-2 and 8uvmo-3 were potent terminators of *C. muridarum* replication, with or without IFN-γ pretreatment of the epithelial monolayer. 8sAg1, 8sAg2, and 8sAg3 were entirely unable to control replication, and IFN-γ pretreatment improved the efficiency of only 8sAg3, and it only modestly. Relative ability to terminate *C. muridarum* replication did not correlate cleanly with IFN-γ produced during interaction with infected epithelial cells (FIG. 4, subpart C).

Example 6

The CD8 Clones have Multifunctional Cytokine Profiles Including Production of IL-13 by Two Clones The cytokine profiles of the CD8 T cell clones were investigated using wells coated with anti-CD3 antibody. 24 h supernatants were collected and analyzed for levels of IL-2, IL-10, IL-13, IL-17, IFN-γ, and TNFα by ELISA (FIG. 3A). All the clones produced significant amounts of IFN-γ and TNFα, with varying amounts of IL-2; three clones produced large amounts of IL-10, and two significant amounts of IL-13: 8uvmo-2 made a trace amount of IL-17. Based on the results of the activated micro array. 8sAg3 was tested for its ability to produce IL-5 (FIG. 3B), and it did in agreement with the micro array data. These multifunctional cytokine patterns do not fall neatly into existing paradigms for CD8 T cell cytokine polarization. IL-13 has been shown to be detrimental to clearance of *Chlamydia muridarum* as determined by genome copy number in mouse lungs and genital tract (Asquith et al. 2013, Plos Path 7:e1001339).

DISCUSSION

CD8 T cell subsets have a role in protection and immunopathology during *Chlamydia* genital tract infections. Experiments utilizing adoptive transfer of *Chlamydia*-specific CD8 T cell lines and clones into chronically infected nude mice demonstrated that CD8 T cells are capable of clearing genital tract infections. Subsequent research utilizing knockout mice revealed that MHC class II (class II knockout) was critical while MHC class I (β2 microglobulin knockout) and CD4 (CD4 knockout) were nonessential for clearing the genital tract. A follow up study using CD4 and CD8 depletions prior to secondary infectious challenge in B cell deficient mice supported the importance of CD4 T cells and identified a role for B cells in clearing *C. muridarum* from the genital tract, without demonstrating a protective effect of *Chlamydia*-specific CD8 T cells that were presumably generated during the primary infection. Those studies did not exclude the possibility that development of protective CD8 T cell immunity is dependent on both CD4 T cells (MHC class II knockout mice) and antibody (T cell depletions in B cell deficient mice). Subsequent research has determined that, on the whole, CD8 T cells contribute to immunopathology more than they do to protection during *Chlamydia* genital tract infections. An important technical hurdle discovered for derivation of CD8 T cell clones in this study was a requirement for immune splenocyte presentation of *Chlamydia* antigens.

Without wishing to be bound by theory, the mechanism underlying the immune splenocytes requirement likely involves one of two known antigen presentation mechanisms. The first is an antigen concentrating mechanism wherein specific antibody efficiently binds and delivers soluble antigen to the pH-dependent endosome/lysosome exogenous pathway for MHC class II presentation. B cells specific for the hapten 2,4,6-trinitrophenyl (TNP) can activate an MHC class II-restricted T cell hybridoma with 1000-fold less TNP-haptenated cognate antigen than naïve B cells. Similarly, IgG specific for tetanous toxoid (TT) improved the efficiency of monocyte-derived dendritic cell activation of TT-specific human CD4 T cell clones by 100-fold. The second mechanism involves delivery of exogenous antigen into an otherwise inaccessible MHC class I presentation pathway. Murine dendritic cells could not cross present physiological concentrations of soluble antigen to an MHC class I-restricted T cell hybridoma, but could cross present IgG-complexed antigen via Fc receptors to the same hybridoma: demonstrating a role for IgG and Fc receptors in directing soluble antigen into an otherwise inaccessible MHC class I presentation pathway. Fc receptors and *Chlamydia* specific antibodies have been shown to play a role in *Chlamydia* pathogenesis. *Chlamydia*-specific antibodies increase the ability of naïve splenocyte APC to activate purified immune T cells to make IFN-γ, and mice deficient in Fc receptors lose their protection from secondary infection. Without wishing to be bound by theory, the defect in secondary immunity may be due to less efficient antigen delivery into the exogenous MHC class II antigen presentation pathway, or loss of an MHC class I cross presentation pathway, or both.

As previously noted, the majority of *Chlamydia*-specific CD8 T cells in this report were not restricted by MHC class Ia molecules. Because 8uvmo-2 and 8uvmo-3 were not activated by naïve splenocytes pulsed with UV-inactivated *C. muridarum*, determination was not made as to their MHC restriction elements. However 8sAg1, 8sAg2, and 8sAg3 were sufficiently activated by antigen-pulsed naïve C57BL/6 and $K^bD^b$ knockout splenocytes to draw the conclusion that they are not restricted by MHC class Ia molecules. This finding in the mouse model is consistent with the finding that the majority of *Chlamydia*-specific CD8 T cell clones isolated from humans with *C. trachomatis* infections were not restricted by HLA class Ia molecules.

*Chlamydia* antigens recognized by CD8 T cells are not fully characterized. Gervassi et al showed that a human class Ia-restricted CD8 clone recognized OmcB, and there is evidence for a human CD8 MOMP epitope. In mice Cap1, CrpA and PmpI were identified as containing CD8 epitopes utilizing mice infected intravenously or intraperitoneally with human *C. trachomatis* serovar L2. A subset of murine CD8 T cells specific for *C. pneumonia* recognized formylated bacterial peptides in the context of H2-M3, an MHC class Ib molecule. Interestingly, a proteomic approach toward identifying T cell epitopes identified only a single *C. muridarum* peptide from amino acid permease (TC_0653) associated with MHC class Ia molecules, while multiple peptide epitopes were extracted from MHC class II molecules. There is no information regarding *C. trachomatis* or *C. muridarum* antigens recognized by non-class Ia restricted CD8 T cells in humans or mice.

The CD8 T cell clones in this study had varying abilities to terminate *C. muridarum* replication in epithelial cells. 8uvmo-2 and 8uvmo-3 were as potent as the most potent *Chlamydia*-specific CD4 T cell clones in a previous study, while 8sAg1, 8sAg2, and 8sAg3 were unable or inefficient at terminating replication, even when the epithelial monolayers were pretreated with IFN-γ. The greater efficiency of 8uvmo-2 and 8uvmo-3 did not correlate cleanly with their relative production of IFN-γ. Efficient termination of *Chlamydia* replication by 8uvmo-2 and 8uvmo-3 may relate to a iNOS-dependent mechanism or cytolysis of infected epithelial cells in the non-infectious reticulate body stage of infection/replication (<18 h post infection for *C. muridarum*).

A notable finding in this study was that 2 of the 5 CD8 T cell clones produced significant amounts of IL-13 upon activation, along with IL-2, IFN-γ, IL-10 and TNFα, IL-13 has been shown to be detrimental to *C. muridarum* clearance from lung and genital tract as IL-13 knockout mice clear infections more quickly than wild type mice. IL-10 is similarly detrimental to *C. muridarum* clearance from lung, and is associated with increased residual scarring. CD8 T cells producing IL-10, IL-13 and TNFα are interesting with respect to immunopathology because in addition to a role for IL-10 in scarring, the combination of TNFα and IL-13 has been shown to induce expression of TGFβ1 in some cell types: this cytokine combination is the underlying mechanism for bleomycin-induced pulmonary fibrosis and TNBS-induced colonic fibrosis in mouse models. Clinical investigations have shown that IL-13 expressing CD8 T cells may mediate immunopathology in systemic sclerosis, a rheumatologic disorder that manifests as progressive scarring of skin. *Chlamydia*-specific CD8 T cells, making IL-10, IL-13 and TNFα, may contribute to the CD8-mediated immunopathology observed in experimental murine genital tract infections. Previous studies in the *C. muridarum* mouse model have shown that CD8 T cells are capable of mediating bacterial clearance from the genital tract: however on the whole, CD8 T cells play a greater role in immunopathology than in protection. CD8 T cells that may contribute to immunopathology, represented by 8sAg1 and 8sAg3, were not restricted by MHC class Ia, were relatively ineffective at terminating *C. muridarum* replication in epithelial cells, and had a cytokine profile including IL-10, TNFα and IL-13, IL-13 production did not cleanly identify poor terminators of *Chlamydia* replication in epithelial cells as IL-13$^{neg}$ 8sAg2 was also ineffective. More importantly, CD8/TNFα-immunopathology has been shown to be a cytokine-mediated event unrelated to bacterial clearance. Because IL-13 and TNFα synergize to induce expression of the scarring-associated cytokine TGFβ in some cell types, IL-13 may play a role in CD8/TNFα-mediated *Chlamydia* immunopathology. A better understanding of CD8 T cells producing IL-13 will likely provide useful insights into *Chlamydia* and systemic sclerosis immunopathology.

Example 7

Human Homolog of Mouse 1810011H11Rik

Patients with systemic sclerosis (scleroderma) were shown to have significant expression of CD8IL-13 biomarker C10orf128, the human homolog of mouse 1810011H11Rik, in their peripheral blood as compared to control patients and patients with acute *Chlamydia* infections (FIG. 9). During acute *Chlamydia* infection CD8IL-3 T cells are localized to the site of infection (i.e. not present in peripheral blood). However, scleroderma is a chronic disseminated inflammatory process: in this setting, there is an expansion of relevant T cell subsets in the peripheral blood.

In a healthy control. C10orf128 positive CD8 T cells are about 0.2% to about 0.4% of the circulating CD8 T cell pool (FIG. 10: see gate P6). Notably, and as extrapolated from the data shown in FIG. 9, the scleroderma patients had C10orf128 mRNA levels as high or higher in their circulating CD8 T cell pool than the healthy controls. The increased C10orf128 mRNA levels in CD8 T cells seen in the original two scleroderma subjects in FIG. 9 appears to reflect the unique presence of CD8IL-13 T cells in the circulating of CD8 T cell pool of scleroderma patients based on the C10orf128 sort-micro array data in FIGS. 11A and 11B and Table 2. At the time of filing, there exists no way to isolate or purify these CD8IL-13 T cells other than pursuant to the methods described herein.

The rabbit antisera used to effectively sort C10orf128 positive CD8 T cells from human blood was made against a peptide having an amino acid sequence comprising QVLAT-GKTPGAEIDFKY (SEQ ID No. 1), or a functional equivalent, variant or fragment thereof. SEQ ID No. 1 is the human homolog of the mouse CD8IL-13 cell surface biomarker 1810011H11Rik predicted extracellular domain. Accordingly, the C10orf128 antibody of the antisera is related to a cell surfaced domain peptide for biomarker C10orf128 and, thus, is capable of recognizing SEQ. ID No. 1, or a functional equivalent, variant or fragment thereof.

Resulting antiserum may be cross absorbed against a scrambled peptide to improve specificity, as it was in this study. Among other things, this C10orf128-specific antisera allows for the development of novel diagnostics and interventions for scleroderma and *Chlamydia* infections. For example, purified C10orf128 positive and negative CD8 T cells from scleroderma patients can now be subjected to gene expression microarray analysis to identify unique targets for scleroderma-specific diagnostics and possible targets for therapeutic interventions.

While various embodiments of compositions and methods hereof have been described in considerable detail, the embodiments are merely offered by way of non-limiting examples. Many variations and modifications of the embodiments described herein % ill be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or to limiting. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that this description and the appended claims will encompass, all modifications and changes apparent to those of ordinary skill in the art based on this disclosure.

---

---

The invention claimed is:

1. A method for identifying the presence or absence of a subset of CD8 T cells that produce interleukin-13 upon activation (CD8IL-13 T cells), the method comprising:
    obtaining or having obtained a sample from a subject comprising a mammal, the sample comprising a population of CD8 T cells;
    quantifying a level of expression of at least a C10orf128 biomarker in the population of CD8 T cells
    comparing the level of expression of the C10orf128 biomarker in the sample to an expression level of such biomarker in a healthy control, wherein if the C10orf128 biomarker in the sample is upregulated relative to the expression level of the relevant healthy control, such upregulation indicative of the subset of CD8IL-13 T cells being present within the population of CD8 T cells; and
    administering or having administered an anti-C10orf128 antibody to the subject.

2. The method of claim 1, wherein:
    the step of quantifying a level of expression of at least a C10orf128 biomarker further comprises quantifying a level of expression of one or more CD8IL-13 T cell biomarkers in the population of CD8 T cells, each of the one or more CD8IL-13 T cell biomarkers selected from a group consisting of: IL-13, IL-5, Arntl, Cep85L, Clc, and Alox5; and further comprising the step of comparing the level of expression of each of the one or more CD8IL-13 T cell biomarkers in the sample to an expression level of such biomarker in a healthy control, wherein if at least one of the one or more CD8IL-13 T cells in the sample is upregulated a predetermined value relative to the expression level of the relevant healthy control, such upregulation is indicative of the subset of CD8IL-13 T cells being present within the population of CD8 T cells.

3. The method of claim 2, wherein the sample comprises blood serum, the subject is a human, and one of the one or more CD8IL-13 T cell biomarkers comprises Clc; and further comprising determining if the blood serum has an elevated expression level of Clc as compared to a healthy control, wherein the elevated blood serum level of Clc is indicative of the human experiencing a rheumatologic disease state.

4. The method of claim 1, wherein the subject comprises a human, the sample comprises peripheral blood, and the anti-C10orf128 antibody further comprises:

a therapeutically effective dose of (a) one or more inhibitors of the C1orf128 biomarker, (b) one or more small molecule inhibitors each formulated to inhibit or deplete the subset of CD8IL-13 T cells in the peripheral blood of the subject, or (c) both (a) and (b).

5. The method of claim 1, wherein the anti-C10orf128 antibody is a monoclonal antibody made against a peptide having an amino acid sequence comprising SEQ ID No. 1 or a functional equivalent, variant, or fragment thereof.

6. The method of claim 1, wherein quantifying a level of expression of at least a C10orf128 biomarker further comprises extracting ribonucleic acid or protein from the population of CD8 T cells and quantifying a level of messenger ribonucleic acid or protein for at least one of the one or more biomarkers in the extracted ribonucleic acid or protein.

7. The method of claim 6, wherein quantifying a level of messenger ribonucleic acid or protein for at least one of the one or more biomarkers is performed using flow cytometry gated on CD8 T cells.

8. The method of claim 1, wherein the step of administering or having administered an anti-C10orf128 antibody to the subject instead comprises administering or having administered a small molecule comprising an Alox5 inhibitor.

9. The method of claim 1, wherein the subject comprises a human, the method further comprises the step of diagnosing the subject with systemic sclerosis if the C10orf128 biomarker in the sample is upregulated relative to the expression level of the relevant healthy control, and the anti-C10orf128 antibody is administered in a therapeutically effective dose, and wherein the antibody comprises antibodies to C10orf128.

10. The method of claim 2:

wherein quantifying a level of expression of the one or more CD8IL-13 T cell biomarkers further comprises using at least one of the one or more CD8IL-13 T cell biomarkers to:

expose the population of CD8 T cells to mitogens or immobilized antibodies made against a T cell receptor complex, and measure (a) a level of IL-5 expression, IL-13 expression, or both in the population of CD8 T cells, (b) a frequency of the subset of CD8IL-13 T cells within the population of CD8 T cells, or (c) both (a) and (b); and further comprising isolating the subset of CD8IL-13 cells within the sample.

11. The method of claim 9, further comprising the step of analyzing a measured parameter following the step of administering or having administered to the diagnosed subject a therapeutically effective dose, the measured parameter relating to a pathophysiology in the diagnosed subject mediated by the subset of CD8IL-13 T cells.

12. The method of claim 1, wherein the subject is a human and the step of administering alternatively or further comprises:

administering or having administered to the subject a therapeutically effective dose of the anti-C10orf128 antibody.

13. The method of claim 11, wherein the pathophysiology in the subject mediated by the subset of CD8IL-13 T cells comprises pathological scarring.

* * * * *

SEQUENCE LISTING

```
<160> NUMBER OF SEQ ID NOS: 2

<210> SEQ ID NO 1
<211> LENGTH: 17
<212> TYPE: PRT
<213> ORGANISM: Artificial Sequence
<220> FEATURE:
<223> OTHER INFORMATION: Human CD8IL-13-specific peptide capable of
      binding the cell surface domain of human CD8IL-13 biomarker
      C10orf128

<400> SEQUENCE: 1

Gln Val Leu Ala Thr Gly Lys Thr Pro Gly Ala Glu Ile Asp Phe Lys
1               5                   10                  15

Tyr

<210> SEQ ID NO 2
<211> LENGTH: 17
<212> TYPE: PRT
<213> ORGANISM: Artificial Sequence
<220> FEATURE:
<223> OTHER INFORMATION: Scrambled version of SEQ ID No. 1

<400> SEQUENCE: 2

Gln Val Leu Ala Asp Ile Glu Ala Gly Pro Thr Lys Gly Thr Tyr Lys
1               5                   10                  15

Phe
```